US008365738B2

(12) United States Patent
Madigan et al.

(10) Patent No.: US 8,365,738 B2
(45) Date of Patent: Feb. 5, 2013

(54) COMBINATION CONDOM AND PERSONAL LUBRICANT CONTAINER

(75) Inventors: Stephen J. Madigan, Dallas, TX (US); Larry Eugene Hess, Lititz, PA (US)

(73) Assignee: Stephen J. Madigan, Flower Mound, TX (US)

( * ) Notice: Subject to any disclaimer, the term of this patent is extended or adjusted under 35 U.S.C. 154(b) by 0 days.

(21) Appl. No.: 13/289,890

(22) Filed: Nov. 4, 2011

(65) Prior Publication Data

US 2012/0048752 A1 Mar. 1, 2012

Related U.S. Application Data

(62) Division of application No. 12/447,255, filed as application No. PCT/US2007/081946 on Oct. 19, 2007, now Pat. No. 8,074,653.

(60) Provisional application No. 60/930,558, filed on May 17, 2007, provisional application No. 60/854,281, filed on Oct. 25, 2006.

(51) Int. Cl.
*A61F 6/04* (2006.01)
*B65D 85/08* (2006.01)

(52) U.S. Cl. .......................................... 128/844; 206/69

(58) Field of Classification Search .................. 128/842, 128/844, 918, 830; 206/69, 364; 604/352, 604/351, 348, 347, 346, 327, 317
See application file for complete search history.

(56) References Cited

U.S. PATENT DOCUMENTS

| 5,117,841 | A | * | 6/1992 | McBeth | 128/844 |
| 5,163,448 | A | * | 11/1992 | Foldesy | 128/844 |
| 6,036,022 | A | | 3/2000 | Young | |
| 6,176,394 | B1 | * | 1/2001 | Shimko et al. | 222/92 |
| 6,213,424 | B1 | | 4/2001 | Helfer-Grand | |
| 6,311,868 | B1 | | 11/2001 | Krietemeier et al. | |
| 6,484,514 | B1 | | 11/2002 | Joseph et al. | |
| 6,581,775 | B1 | | 6/2003 | Hagopian | |
| 6,612,427 | B2 | | 9/2003 | Woodhouse | |
| 6,694,980 | B2 | | 2/2004 | Anderson | |
| 6,742,521 | B2 | | 6/2004 | McCleskey et al. | |
| 6,911,010 | B2 | | 6/2005 | Dirks et al. | |
| 7,021,064 | B2 | | 4/2006 | Wohland et al. | |
| 2005/0045497 | A1 | * | 3/2005 | Sample | 206/69 |

FOREIGN PATENT DOCUMENTS

WO 95/02379 A1 1/1995

OTHER PUBLICATIONS

European Search Report EP 07872327.7 dated Feb. 2, 2010.
International Search Report and Written Opinion for PCT/US2007/81946 dated Jun. 18, 2008.

* cited by examiner

*Primary Examiner* — Loan Thanh
*Assistant Examiner* — Tarla Patel
(74) *Attorney, Agent, or Firm* — Chalwalker Flores, LLP; Daniel J. Chalker

(57) ABSTRACT

The present invention comprises articles of manufacture including a disposable condom and personal container comprising a condom compartment enclosing one or more condoms immersed in either a personal lubricant or sexually stimulating lubricant removably adjoined to at least one lubricant compartment. The compartments are constructed of a packaging material comprising properties that conduct heat and hermetically sealed. The condom compartment comprises a seal positioned on the top wall that is removed or opened for the purpose of gaining access to the contents. The personal lubricant compartment comprises a discharge element through which the contents of the compartment are discharged by activating a removable dispenser that fits within the element. The contents of the compartments may be heated by a device in which the compartments are seated. The temperature of the contents may be monitored with the aid of a temperature sensing aid.

15 Claims, 17 Drawing Sheets

COMBINATION CONDOM AND PERSONAL LUBRICANT CONTAINER

PRIORITY CLAIM

This patent application is a divisional patent application of U.S. patent application Ser. No. 12/447,255 filed on Apr. 25, 2009 and entitled "Combination Condom and Personal Lubricant Container," which is a Section 371 U.S. national phase application of PCT/US07/81946 filed on Oct. 19, 2007, which claims priority to U.S. provisional patent application Ser. Nos. 60/930,558 filed on May 17, 2007 and 60/854,281 filed on Oct. 25, 2006, all of which are hereby incorporated by reference in their entirety.

FIELD OF THE INVENTION

This invention relates to a disposable container comprising a first compartment enclosing one or more condoms and a personal lubricant in which said one or more condoms are immersed, hereinafter referred to as a condom compartment, and at least one other compartment enclosing personal lubricant, hereinafter referred to as a personal lubricant compartment, and a kit comprising at least one condom compartment and at least one associated personal lubricant compartment. In the case of the disposable container the condom compartment is removably adjoined to at least one personal lubricant compartment. The compartments are constructed of a packaging material comprising properties that conduct heat such as aluminum. Each compartment comprises multiple walls hermetically sealed forming an airtight enclosure in which the contents reside. Each compartment comprises an element that aids in the removal of its contents preferably after being heated to a desired temperature by a device in which at least one compartment or the container is seated. In lieu of personal lubricant, the compartments may enclose a sexually stimulating lubricant.

BACKGROUND OF THE INVENTION

Containers or kits have been configured to house a condom and liquid material used prior to, in, or after sexual activities. A device has been developed to house a condom and liquid material said device comprising a means to dispense the liquid material. Devices have been developed comprised of an element that heats liquid material contained therein prior to extraction using an exothermic or electric heat source. A device has been developed comprised of an element that heats a liquid material contained therein but only after the liquid material is dispensed on a target area. A device has been developed to house articles to be dispensed but only after a liquid material contained within the device is applied to an article and heated prior to dispensing the moistened, heated article. The prior art hereinafter discussed is limited to articles of manufacture that house one or more condoms, a liquid material used in sexual activities or a condom and a liquid material used in sexual activities and devices that heat a liquid material contained therein either prior to or after removal of the liquid material or heat a pre-moistened article contained within the device prior to removal of the article from the device.

U.S. Pat. No. 6,742,521 B2 issued in June of 2004 to McCleskey et al., titled "Combination Prophylactic and Sanitizer," principally describes an invention combining a packaged prophylactic with a packaged sanitizer. The McCleskey invention claims a combination prophylactic and sanitizer comprising at least one disposable package containing at least one prophylactic and at least one disposable package containing at least one sanitizer said packages may be removably secured to each other. An alternative embodiment of the McCleskey invention claims a separate package used as a receptacle into which used/contaminated prophylactics or sanitizers are placed.

The McCleskey invention combines at least one disposable package containing at least one prophylactic and at least one disposable package containing at least one sanitizer. The term "sanitizer" is defined in the McCleskey specification. A sanitizer is a disposable towelette, napkin, wipe, and/or swab pre-moistened with a sterilizing agent, lubricant, or spermicidal. The specification further provides that although a sanitizer is preferably a premoistened towelette, it is contemplated in an alternate embodiment that a sanitizer may be a self-contained liquid/gel sterilizing agent (without towelette). However, the specification does not provide that a sanitizer may be a self-contained liquid used in sexual activities (without towelette) other than a self-contained liquid/gel antiseptic or sterilizing agent The present invention discloses multiple disposable compartments each compartment enclosing a liquid material, such as personal lubricant. The liquid material residing in either compartment is self-contained, that is, without towelette. An element of the McCleskey invention, a packaged sanitizer, as defined in the specification, is not an element of the present invention.

The McCleskey specification provides that a prophylactic or sanitizer within a package is manually removed after tearing open the package. The present invention provides that the contents of the condom compartment are manually removed after removing or opening a seal comprising the compartment while the contents of the personal lubricant are mechanically removed with the aid of a removable dispenser positioned within a discharge element of the compartment. In an alternate embodiment the contents of the personal lubricant are removed with the aid of a permanently attached dispenser. An element of the McCleskey invention, manual removal of the contents contained within both packages, is not an element of the present invention.

The McCleskey invention discloses a means to manually reseal a package that contains or contained at least one sanitizer or a receptacle designed to hold used/contaminated prophylactics or sanitizers/towelettes. The McCleskey invention does not provide a means to reseal a package containing at least one prophylactic. The present invention discloses a means to reseal each compartment. If the seal comprising the condom compartment is removed or opened, the seal may be manually reattached or closed. If the seal within the discharge element comprising the personal lubricant compartment is ruptured, the open end of the discharge element may be resealed mechanically with the aid of a dispenser or manually with a cap. Thus, the present invention comprises an element that is not an element of the McCleskey invention, i.e., the condom compartment may be resealed manually whereas the package containing at least one prophylactic is not resealed. Also, an element of the McCleskey invention is not an element of the present invention, i.e., a package containing a sanitizer may be manually resealed whereas the personal lubricant compartment is resealed mechanically or manually.

The McCleskey specification provides that a package containing a prophylactic or sanitizer may be formed from any suitable packaging material including aluminum, plastic, or paper. The present invention comprises a multiple compartments that are formed from a packaging material comprised of properties that conduct heat such as aluminum. The contents of the compartments are heated prior to removal or discharge. An element of the McCleskey invention, packages containing prophylactics or sanitizers may be constructed from material that does not conduct heat, is not an element of the present invention.

The McCleskey invention comprises multiple two-sided packages. The drawings do not support an embodiment of the invention comprising packages with more than two walls. The present invention comprises compartments with at least three walls. An element of the McCleskey invention, multiple two-sided packages, is not an element of the present invention.

The McCleskey invention comprises a package containing at least one prophylactic. The specification makes no mention of a liquid material enclosed within the package other than that contained in a conventional package. The present invention discloses a container or kit comprising a condom compartment enclosing one or more condoms and a liquid material such as personal lubricant, in which the one or more condoms are immersed. An element of the McCleskey invention, a package containing only one or more prophylactics, as defined in the specification, is not an element of the present invention.

U.S. Pat. No. 6,581,775 B1 issued in June of 2003 to Hagoplan, titled "Method of External Genital Cleansing and Prophylactic Kit," describes a kit comprised of a sealed container housing one or more packaged condoms and one or more packaged wipes having topical microbicides, personal lubricants, sterile water, or sterile water-based solution disposed on or impregnated therein. The articles comprising the kit are principally used to avoid the transmission of disease during sexual intercourse, to provide a lubricating aid during sexual intercourse, and to externally cleanse the genitals prior to or after sexual intercourse. The articles comprising the kit are available over the counter. The present invention does not include each element of the Hagoplan invention.

U.S. Pat. No. 6,612,427 B2 issued in September of 2003 to Woodhouse, titled "Method and Apparatus for Containing Prophylactic Articles," describes a sanitary nondisposable container for storing one or more prophylactics. The container is comprised of a convex compartment, a recessed compartment, and a hinge that permits the compartment to mate forming an airtight seal. An unpackaged prophylactic is situated between the two compartments when the container is in a closed position. Although not claimed, the specification provides that a sanitary compartment may be added that houses a personal lubricant. The present invention does not include each element of the Woodhouse invention.

U.S. Pat. No. 6,694,980 B2 issued in February of 2004 to Anderson, titled "Prophylactic Garment System for Safer Sex," describes an undergarment worn while performing sexual activities comprising an opening in the crouch area facilitating intercourse and one or more pockets used to store sexual aids, including a packaged condom or packaged personal lubricant. The sexual aids are intended to be individually purchased over the counter. The present invention does not include each element of the Anderson invention.

U.S. Pat. No. 6,036,022 issued in March of 2000 to Young, titled "Combination Condom Case and Fragrance Dispenser," describes a combination condom case and fragrance dispenser. The Young invention comprises a portable non-disposable container comprising a compartment that contains a condom or condoms and a compartment that contains a fragrance or perfume tube. The fragrance or perfume contained in the tube is dispensed through an opening in the front wall by means of depressing a plunger located on the top wall. The condom or condoms housed in the device are individually purchased over the counter. The present invention does not include each element of the Young invention.

U.S. Pat. No. 5,163,448 issued in November of 1992 to Foldesy, titled "Condom Comprising Dispensing Structure and Method of Making and Using the Same," describes a condom comprising openings on its proximal portion said condom rolled onto a roll ring containing a liquid material and as the roll ring is squeezed the liquid material exudes out through the openings of the condom. The present invention does not include each element of the Foldsey invention.

U.S. Pat. No. 6,484,514 B1 issued in November of 2002 to Joseph et al., titled "Product Dispenser Having Internal Temperature Changing Element," describes a temperature modifying system for heating a product within a flexible container using an exothermic element also contained within the flexible holder. The heat from the exothermic element is released when pressure is applied to the outside of the flexible container causing the internal element to rupture. The product dispensed is heated as a result. The present invention comprises compartments that are not exothermically heated. The present invention does not include each element of the Joseph invention.

U.S. Pat. App. No. 2004/0194472 A1 published in October 2004 by Wohland et al., titled "Multi-Compartment Pack for Cooling or Heating of Products," describes a multi-compartment pack comprising a product contained within a compartment that is exothermically heated before being removed and two other compartments containing the components that create the chemical reaction resulting in exothermic heat. The present invention comprises compartments that are not exothermically heated. The present invention does not include each element of the Wohland patent application.

U.S. Pat. No. 6,311,868 B1 issued in November of 2001 to Krietemeier et al., titled "Dispenser Which Incrementally Heats Fluids with Substantial Non-Volatile Constituent Parts," describes a device that houses a large quantity of liquid material then transfers a portion of the liquid material to a pre-delivery chamber where it is heated to a desired temperature finally dispensing the liquid material by means of a dispensing spout. The device is AC or DC powered. The present invention does not include each element of the Krietemeier invention.

U.S. Pat. No. 6,911,010 B2 issued in June of 2005 to Dirks et al., titled "Heated Massager with Massaging Liquid Dispenser," describes a hand-held battery powered vibrating massager comprising a heated vibrating body contacting element, and a sealed container of massaging liquid. The dispensed massaging liquid is heated on the target surface by means of the body contacting element. The present invention does not include each element of the Dirks invention.

U.S. Pat. No. 6,213,424 B1 issued in April of 2001 to Helfer-Grand, titled "Towelette Dispenser Apparatus," describes a portable device that dispenses pre-moistened heated towelettes. The towelettes may be housed originally in the dispenser dry and moistened as dispensed or originally housed in the dispenser in a pre-moistened state. In either case the towelette is heated as dispensed. The portable dispenser if AC or DC powered. The present invention does not include each element of the Helfer-Grand invention.

SUMMARY OF THE INVENTION

The primary object of the invention is to encourage the use of condoms in sexual activities thereby reducing the spread of disease, including the human immunodeficiency virus (HIV), which may result in AIDS, and reducing the risk of pregnancy. The invention discloses a disposable container comprising a condom compartment enclosing one or more condoms immersed in a liquid material such as personal lubricant, removably adjoined to at least one personal lubricant compartment enclosing a liquid material such as personal lubricant, and a kit comprising at least one condom compartment and at least one associated personal lubricant compartment. Prior to their removal, the contents of the condom compartment are heated by a device in which the compartment is seated. A condom substantially more lubricated than a typical packaged condom is easier to don. Also, the donning of a warm condom that has been a heated by a liquid material in which it is immersed is more sensually pleasing than donning a typical packaged condom. The portion of personal lubricant contained in the opened compartment, now warm, may be applied to the penis further facilitating the donning of the condom.

Another object of the invention is to package a condom and a liquid material such as personal lubricant in a single compartment or container comprising multiple compartments. By packaging a condom with a popular sexual aid, such as personal lubricant, use of condoms will be encouraged as both are immediately available.

Another object of the invention is to market an article of manufacture containing items used in sexual activities that is tamper-proof and meets the highest of standards for personal hygiene. As regards tampering, the compartments are hermetically sealed. The condom compartment comprises a seal located on the top wall. When the seal is opened, the contents of the condom compartment are exposed and manually accessible. The personal lubricant compartment comprises a discharge element comprising multiple seals. The contents within the personal lubricant compartment are accessed and mechanically discharged after rupturing a protective seal within the discharge element presumably with the piercing element of a removable dispenser. Preferably, a cap covering the discharge element is removed prior to rupturing the protective seal. Alternatively, the contents of the compartment are removed with the aid of an permanently attached dispenser. As regards personal hygiene, safeguards have been included which reduce the risk that liquid material contained in any previously accessed compartment will not migrate out. The condom compartment has two built-in safeguards. First, an opened condom compartment may be resealed by reattaching or closing the seal to the top wall. Second, a raised annular ring positioned on the top wall of the condom compartment provides a barrier to the migration of liquid material out of the compartment and into the heating mechanism of a warming device in which the compartment is seated. The personal lubricant compartment has built-in safeguards. First, a cap may be re-installed to the end of the discharge element. Second, the discharge element is sized to accommodate a removable dispenser that fits snugly within the element avoiding leakage. Finally, compartments comprising a container may be detached from one another. A previously accessed compartment may be detached avoiding a mess not otherwise solved.

The primary advantage of the invention is that a liquid material, such as personal lubricant, may be heated to a temperature that exceeds body temperature. Warm personal lubricant applied to the skin results in greater pore penetration than a personal lubricant applied to the skin at a temperature well below body temperature. The application of warm personal lubricant avoids the shock associated with a personal lubricant that has not been heated to a temperature that exceeds body temperature. The temperature of the liquid material enclosed within a compartment may be monitored with the aid of a temperature sensor known in the art when the container is seated in a warming device.

Another advantage of the invention is to reduce waste. A container comprises multiple compartments adjoined to one another. The compartments may be detached from one another with the aid of perforations in the container. If either compartment has been depleted, the depleted compartment may be removed and discarded without discarding the full or partially depleted compartment. Also, the user of the invention determines the amount of liquid material to be removed or dispensed from a compartment not possible with a single use package containing a limited amount of the liquid material.

Another advantage of the invention is to avoid the mess associated with removing a liquid material from a disposable package by tearing an edge. Opening such a package is often difficult particularly if the quantity of liquid material within a first package was insufficient and a second package is being opened with lubricated hands. The contents of the personal lubricant compartment are dispensed using a dispenser.

Another advantage of the invention is that condoms, personal lubricant or sexually stimulating lubricant known in the art are used. The condom is preferably a male condom. Personal lubricant includes a lubricant sold under the brand name KY, Durex, Astroglide, Liquid Silk, among others, and is not limited to water-based lubricants.

The present invention relates to disposable container comprising a condom compartment enclosing one or more condoms and a personal lubricant in which said one or more condoms are immersed, removably adjoined to at least one personal lubricant compartment enclosing a personal lubricant, and a kit comprising at least one condom compartment and at least one associated personal lubricant compartment. In lieu of personal lubricant, the compartments may enclose a sexually stimulating lubricant. The condom compartment is constructed of a packaging material containing properties that conduct heat such as aluminum, is three-dimensional in shape including but not limited to a cylindrical or rectangular shape, is hermetically sealed, and may be associated with or removably adjoined to a personal lubricant compartment. The personal lubricant compartment is constructed of a packaging material containing properties that conduct heat such as aluminum, is three dimensional in shape including but not limited to a funnel shape, is hermetically sealed, and may be associated with or removably adjoined to a condom compartment. The contents of the condom compartment are manually accessed by removing or opening a seal positioned atop the compartment. The seal may be re-attached or closed to avoid spillage or waste. The condom compartment may comprise a raised annular ring positioned on the top of the compartment providing an additional barrier to the migration of liquid material. The contents of the personal lubricant compartment are accessed by rupturing a protective seal within a discharge element comprising the compartment. The contents are then discharged through the discharge element by activating a removable dispenser that fits snugly within the discharge element. Alternatively, the contents of the compartment are removed with the aid of a permanently attached dispenser. The contents of the compartments may be heated prior to being removed or discharged by a device in which the compartments are seated. The temperature of the contents may be monitored with the aid of a temperature sensing aid. When the condom compartment comprises a part of a container, it is positioned at the distal end (in relation to the point of discharge of the contents from the second compartment) of the container while the personal lubricant compartment is positioned at the proximal end of the container. The container comprises perforations the means used to detach the compartments. In lieu of a single personal lubricant compartment, a container may comprise two congruent compartments, each compartment adjoined to the condom compartment and positioned on opposing ends of the container.

BRIEF DESCRIPTION OF THE DRAWINGS

The above and further advantages of the invention may be better understood by referring to the following description in conjunction with the accompanying drawings, in which.

DETAILED DESCRIPTION OF THE INVENTION

Figure 1:
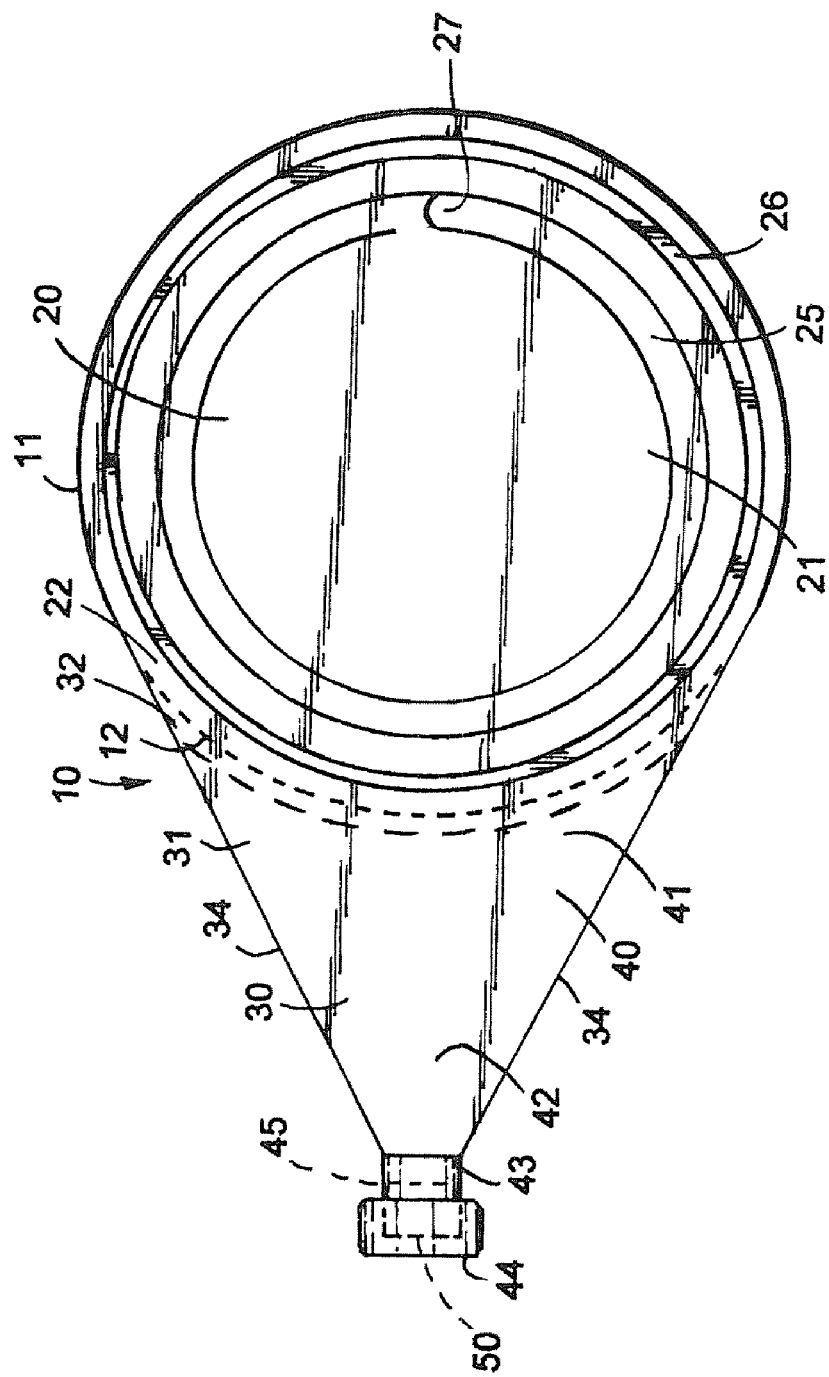
FIG. 1 shows the first of three top views of a first embodiment of a combination condom and personal lubricant container.

First Embodiment of Combination Condom and Personal Lubricant Container—FIGS. 1, 2, 3, 4, 5, 6

FIGS. 1-6 show various views of a first embodiment of article of manufacture comprising a condom compartment 20 removably adjoined to a personal lubricant compartment 30 hereinafter referred to as a combination condom and personal lubricant container 10. The container 10 is disposable. The compartments 20, 30 comprising the container 10 are constructed of a flexible, semi-rigid, or rigid packaging material 11 comprising properties that conduct heat, such as aluminum. The compartments are adjoined to one another at a protruding curved edge of the top wall of each compartment 22, 32 forming a common border. The compartments 20, 30 may be permanently separated from one another with the aid of perforations in the top of the container 12 arranged in a curved pattern along the common border.

Figure 2:
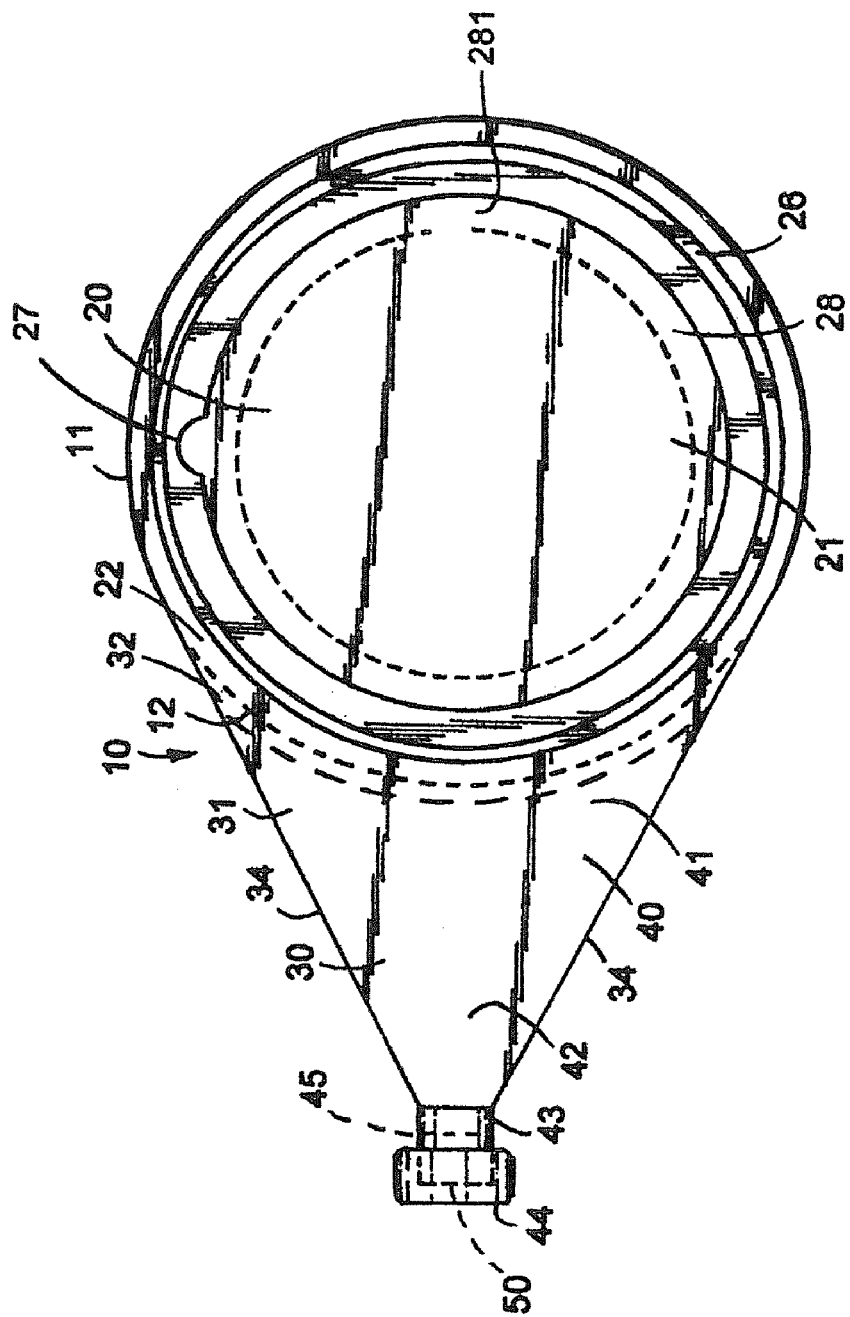
FIG. 2 shows the second of three top views of a first embodiment of a condom and personal lubricant container.
Figure 3:
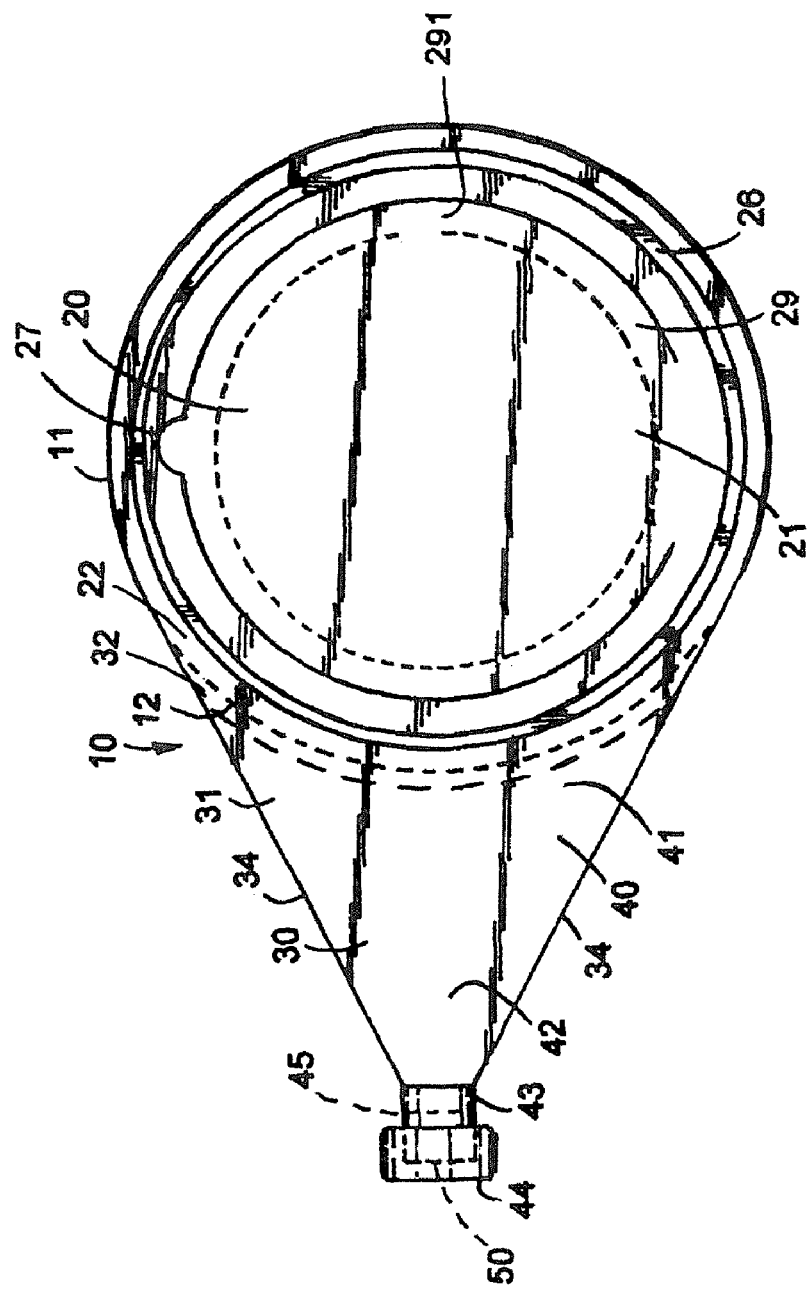
FIG. 3 shows the third of three top views of a first embodiment of a condom and personal lubricant container.

FIGS. 1, 2 and 3 discussed below each show a top view of the first embodiment of the combination condom and personal lubricant container 10. In each drawing the top wall of the condom compartment 21 is shown to comprise a different seal, in design and function. Descriptions of the first embodiment of the combination condom and personal lubricant container 10 shown in FIGS. 2 and 3 are limited to descriptions of the particular seal 28, 29.

FIG. 1 shows the first of three top views of the first embodiment of the combination condom and personal lubricant container 10. The condom compartment 20 is positioned at the distal end (in relation to the point of discharge 50 of the contents in the personal lubricant compartment 30) of the container 10. The top view shows the top wall of the condom compartment 21 to be oval shaped. The top wall 21 comprises a removable seal 25. The drawing depicts a removable seal 25 in the shape of an annular strip with a tab 27. By pulling the tab 27 and removing the seal 25, the contents are accessed and may be manually removed. The seal 25 may not be reattached. The top wall of the condom compartment 21 also comprises a protruding curved edge 22 extending out the entire perimeter of the top wall 21. Preferably, the top wall of the condom compartment 21 also comprises a raised annular ring 26. The raised annular ring 26 is positioned between the perimeter of the top wall of the compartment 21 and the removable seal 25. The raised annular ring 26 provides a barrier to the migration of liquid material contained in an open condom compartment 20 when the container 10 is seated in a device used to heat its contents. The raised annular ring 26 helps prevent liquid material from entering the part of a device that heats the contents of the compartments 20, 30.

The personal lubricant compartment 30 is positioned at the proximal end of the container 10. The personal lubricant compartment 30 is in the shape of a funnel 40. The top wall of the personal lubricant compartment 30 comprises a protruding curved edge 32 extending away from a curved interior side wall 35 (shown by a dashed line). The protruding curved edge 32, two side walls 34 (top edge only shown) separated by a discharge element 43 and the discharge element 43 mark the perimeter of the top of the compartment 30. The top 30 wall of the compartment 31 is tapered sloping downward away from the curved interior side wall 35, the broad end of the funnel 41, and terminating at the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 30. Personal lubricant discharged is, for the most part, gravity fed. The narrow end of the funnel 42 comprises an open-ended discharge element 43 or fitting designed to receive a removable dispenser. Before discharging the contents, a protective seal 45 (shown by a dashed line) within the discharge element 43 is ruptured presumably with a piercing element of a removable dispenser. The discharge element 43 may also comprise a cap 44 that must be removed from the end of the element 43 before rupturing the protective seal 45.

FIG. 2 shows the second of three top views of the first embodiment of the combination condom and personal lubricant container 10. The discussion set forth in this paragraph is limited to the design of the seal. The top wall of the condom compartment 21 comprises a removable re-attachable seal 28 comprising a tab 27 and a circular support for a re-attachable seal 281, in lieu of a removable seal 25 that is not re-attachable. The drawing depicts an oval-shaped seal 28. By pulling the tab 27 and removing the seal 28, the contents of the compartment 20 are accessed and may be manually removed.

The seal 28 may be re-attached to the top wall of the compartment 21 by pressing the seal against the circular support for a re-attachable seal 281. By re-attaching the seal 28, the remaining contents of the compartment 20 are hygienically secured avoiding spillage. The underside of a reattachable seal 28 and top of a circular support for a re-attachable seal 281 comprise an adhesive to secure one to the other; however, other securing means known in the art may be used.

FIG. 3 shows the third of three top views of the first embodiment of the combination condom and personal lubricant container 10. The discussion set forth in this paragraph is limited to the design of the seal. The top wall of the condom compartment 21 comprises a partially affixed seal 29 comprising a tab 27 and a circular support for a partially affixed seal 291, in lieu of a removable seal 25 that is not re-attachable. The drawing depicts an oval shaped seal 29. The partially affixed seal 29 is opened and closed without removing the seal 29 from the top wall of the compartment 21. By pulling the tab 27 and opening the seal 29, the contents of the compartment 20 are accessed and may be manually removed. The seal 29 may be closed by pressing the seal 29 against the circular support for a partially affixed seal 291. By closing the seal 29, the remaining contents of the compartment 20 are hygienically secured avoiding spillage. The underside of a partially affixed seal 29 and top of the circular support for a partially affixed seal 291 comprise an adhesive to secure one to the other; however, other securing means known in the art may be used.

Figure 4:
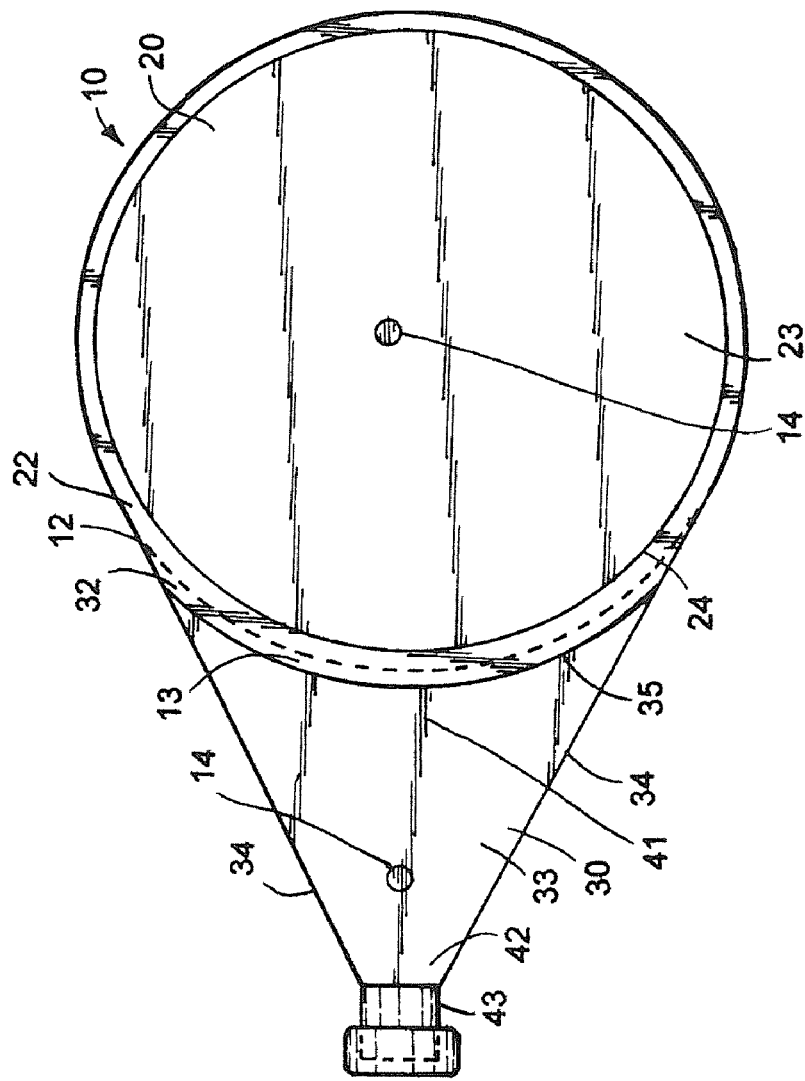
FIG. 4 shows a bottom view of a first embodiment of a combination condom and personal lubricant container.

FIG. 4 shows a bottom view of the first embodiment of a combination condom and personal lubricant container 10. The perforations in the top of the container 12 and the protruding curved edge of the top wall of each compartment 22, 32 are in view.

The condom compartment 20 is positioned at the distal end of the container 10. A cylindrical wall 24 (bottom edge only shown) marks the perimeter of a bottom wall of the compartment 23. A portion of the cylindrical wall 24 faces a curved interior side wall of the personal lubricant compartment 35 (bottom edge only shown). The bottom wall of the condom compartment 23 is substantially flat. The bottom wall of the compartment 23 may comprise a temperature sensing aid 14. The temperature sensing aid 14 allows the temperature of the contents enclosed within the compartment 20 to be monitored when the contents of the compartment 20 are heated by a device in which the container 10 is seated. The temperature sensing aid 14 may be a temperature sensor known in the art or a component known in the art that makes contact with a temperature sensor a part of the heating device.

The personal lubricant compartment 30 is positioned at the proximal end of the container 10. The curved interior side wall 35 (bottom edge only shown), two side walls 34 (bottom edge only shown) separated by the discharge element 43, and the discharge element 43 mark the perimeter of the bottom of the compartment 30. The curved interior side wall of the compartment 35 faces the cylindrical wall of the condom compartment 24. The bottom wall of the compartment 33 is tapered and horizontally positioned in the container 10 and extends away from the bottom horizontal edge of the curved interior side wall 35, the broad end of the funnel 41, toward the discharge element 43, the narrow end of the funnel 42. The bottom wall of the compartment 33 may comprise a temperature sensing aid 14. The temperature sensing aid 14 allows the temperature of the contents enclosed within the compartment 30 to be monitored when the contents of the compartment 30 are heated by a device in which the container 10 is seated. The temperature sensing aid 14 may be a temperature sensor known in the art or a component known in the art that makes contact with a temperature sensor a part of the heating device.

The drawing discloses a curved space 13 between the cylindrical wall of the condom compartment 24 and the curved interior side wall of the personal lubricant compartment 35 which may accommodate a heating element of the warming device.

Figure 5:
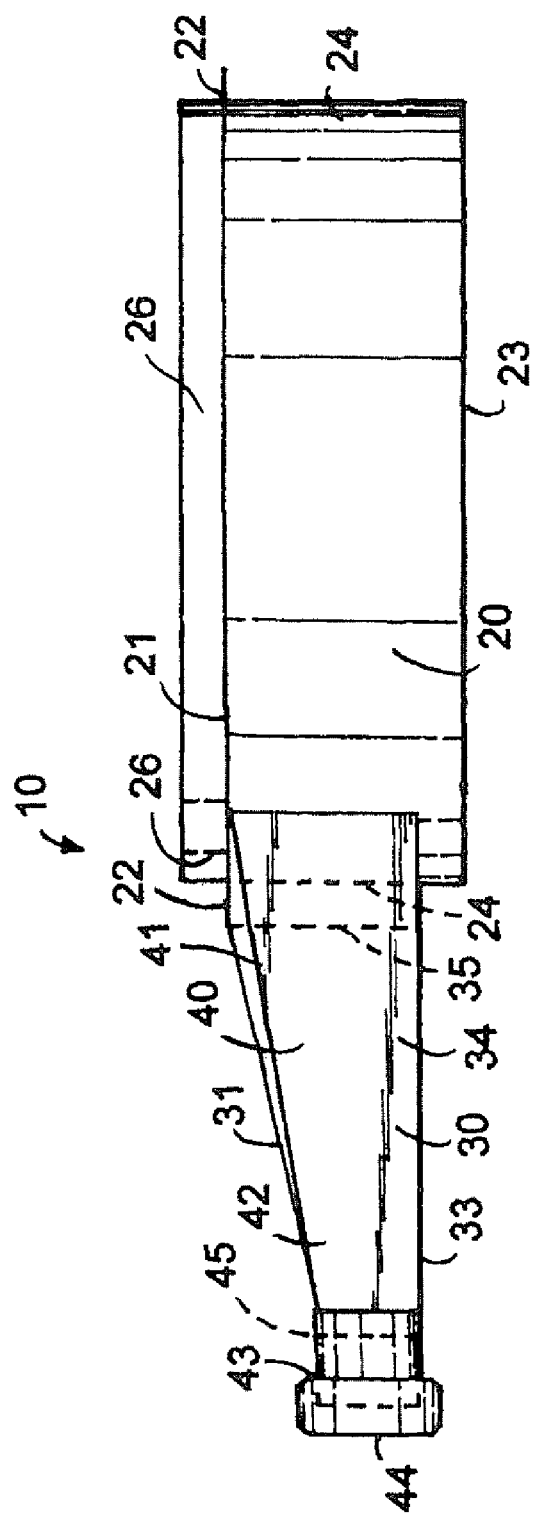
FIG. 5 shows a side view of a first embodiment of a combination condom and personal lubricant container.

FIG. 5 shows a side view of the first embodiment of the combination condom and personal lubricant container 10.

The drawing favors the length of the container 10. The condom compartment 20 is positioned at the distal end of the container 10. The condom compartment 20 comprises a substantially flat top wall 21 (edge only shown) and bottom wall 23 (edge only shown) parallel to one another and a cylindrical wall 24 perpendicular to the top wall 21 and bottom wall 23 said walls hermetically sealed to form an airtight enclosure in which the contents reside. The cylindrical wall 24 faces the curved interior side wall of the personal lubricant compartment 35. The top wall of the compartment 21 comprises the protruding curved edge 22 and, preferably, the raised annular ring 26. The cylinder-shaped condom compartment 20 is deep enough to accommodate one or more condoms and a personal lubricant or sexually stimulating lubricant in which said one or more condoms are immersed.

The personal lubricant compartment 30 is positioned at the proximal end of the container 10. The drawing favors the length of the container 10. The compartment 30 is in the shape of a funnel 40. The top wall of the compartment 31 comprises a protruding curved edge 32 extending away from the curved interior side wall 35. The compartment comprises a sloping top wall 31, a horizontally positioned bottom wall 33 (side edge only shown), two tapered side walls 34 (only one wall shown), and the discharge element 43, the taper terminus for said walls. The compartment 30 also comprises a curved interior side wall 35 marking the broad end of the funnel 41. The curved interior side wall 35 is joined to the top wall 31, bottom wall 33, and each side wall 34 at its top horizontal edge, bottom horizontal edge, and vertical edge, respectively. Said walls and discharge element 43 are hermetically sealed to form an airtight enclosure in which the contents reside. The top wall of the compartment 31 slopes downward diagonally away from the top horizontal edge of the curved interior side wall 35, the broad end of the funnel 41, toward the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 30. Personal lubricant discharged is, for the most part, gravity fed. The discharge element 43 is open-ended and designed to receive a removable dispenser. Before discharging the contents, a protective seal 45 within the discharge element 43 is ruptured presumably with a piercing element of a removable dispenser. The discharge element 43 may also comprise a cap 44 that must be removed from the end of the element 43 before rupturing the protective seal 45.

Figure 6:
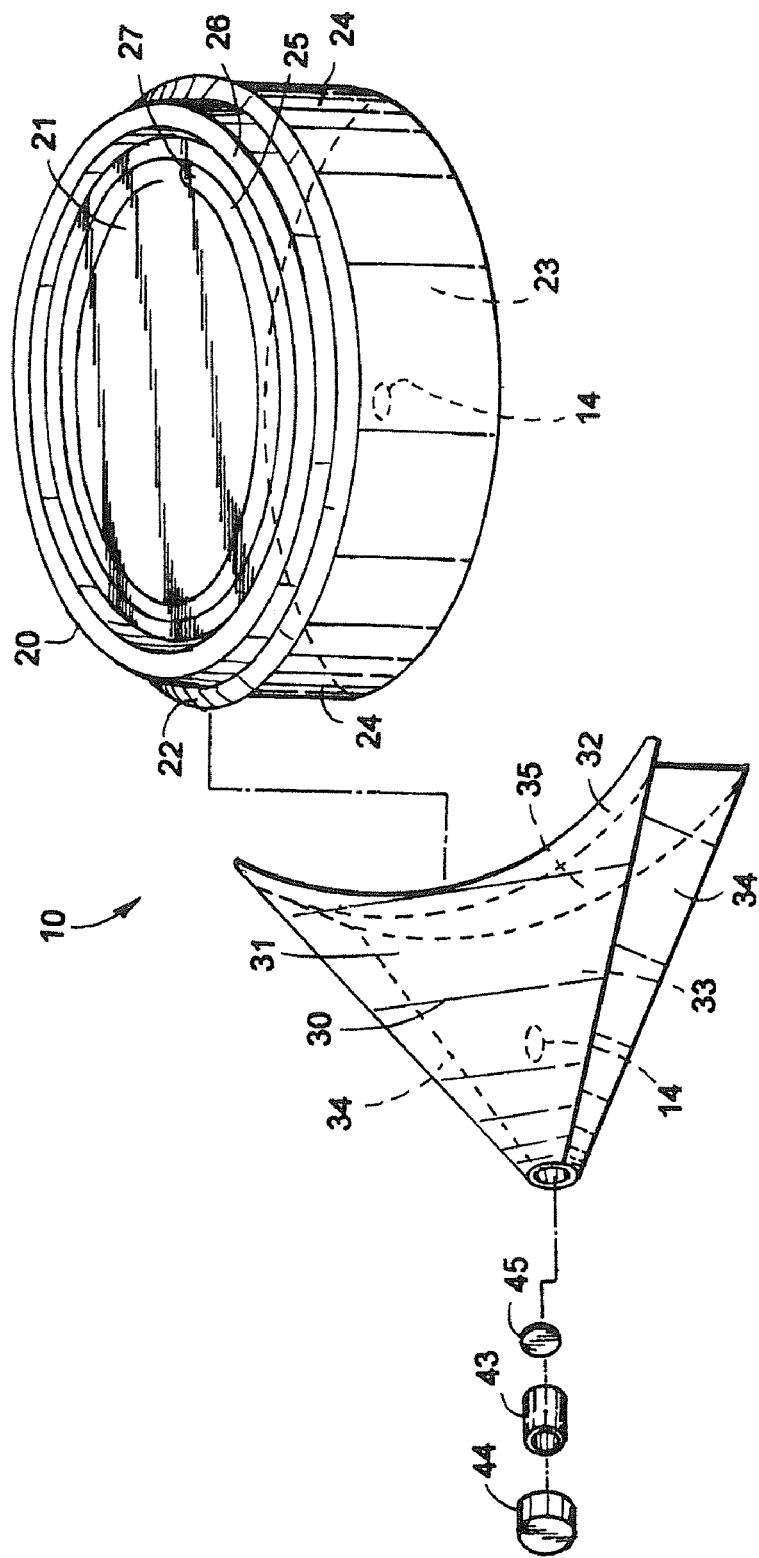
FIG. 6 shows an exploded view of a first embodiment of a combination condom and personal lubricant container.

FIG. 6 shows an exploded view of the first embodiment of the combination condom and personal lubricant container 10. The condom compartment 20 and personal lubricant compartment 30 are separated from another with the aid of perforations in the container 12. The condom compartment 20 is shown to comprise a top wall 21 comprising a removable seal 25 in the shape of an annular strip with a tab 27, a protruding curved edge 22 and a raised annular ring 26 positioned between the seal 25 and the protruding curved edge 22 and a cylindrical wall 24. A bottom wall 23 is hidden but the temperature sensing aid 14 comprising the bottom wall 23 is shown by a dashed oval. In lieu of a removable seal 25, the top wall of the compartment may comprise a removable re-attachable seal 28 (not shown) or a partially affixed seal 29 (not shown). Although the drawing depicts the top wall 21 comprising the raised annular ring 26 and the hidden bottom wall comprising a temperature sensing aid 14, these elements are only preferred. The personal lubricant compartment 30 is shown to comprise a discharge element 43 which is separated from the compartment 30 at the narrow end of the funnel 42. A cap 44 and protective seal 45 are separated from the discharge element 43. The discharge element 43 is an open-ended fitting shown to be cylindrical in shape. The three dimensional shape of the condom compartment 20 and personal lubricant compartment 30 defines the volume of the contents contained therein.

Second Embodiment of a Combination Condom and Personal Lubricant Container—FIGS. 7, 8, 9, 10

FIGS. 7-10 show various views of an article of manufacture comprising a condom compartment 20 removably adjoined to congruent personal lubricant compartments 130, 150 hereafter referred to as a combination condom and personal lubricant container 110. The container 110 is disposable. The compartments 20, 130, 150 comprising the container 110 are constructed of a flexible, semi-rigid, or rigid packaging material 11 comprising properties that conduct heat such as aluminum. The condom compartment 20 positioned in the center of the container 110 is removably adjoined to congruent personal lubricant compartments 130, 150 flanking the condom compartment at a protruding curved edge of the top wall of each compartment 22, 132, 152 forming a common border. The congruent compartments 130, 150 may be detached from the condom compartment 20 with the aid of perforations in the top of the container 112 arranged in two curved patterns along the common border.

Figure 7:
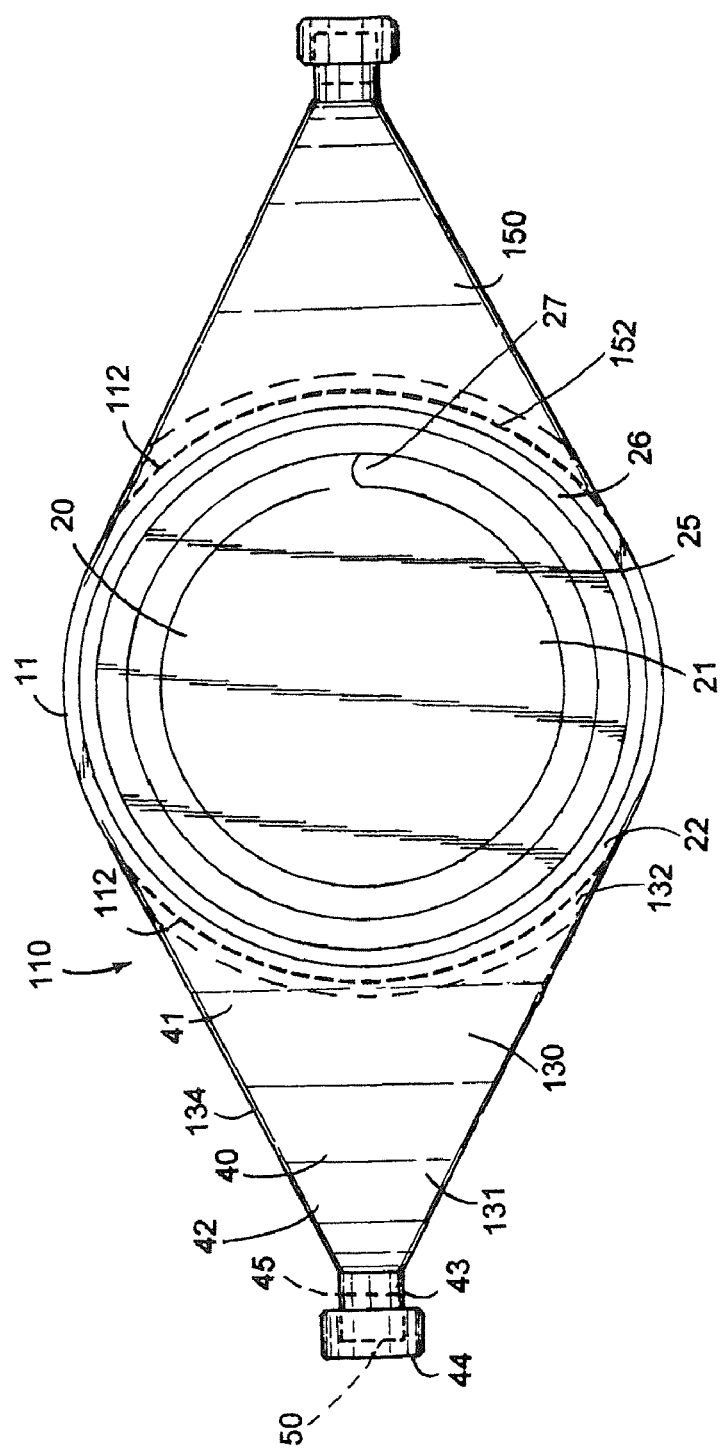
FIG. 7 shows a top view of a second embodiment of a combination condom and personal lubricant container.

FIG. 7 shows a top view of the second embodiment of the combination condom and personal lubricant container 110. The condom compartment 20 is positioned at or near the center of the container 110. The protruding curved edge of the top wall 22 marks the perimeter of the top wall of the compartment 21. The top wall of the condom compartment 21 comprises a removable seal 25. The drawing depicts a removable seal 25 in the shape of an annular strip with a tab 27. By pulling the tab 27 and removing the seal 25, the contents are accessed and may be manually removed. The seal 25 may not be reattached. In lieu of a removable seal 25, the top wall of the condom compartment 21 may comprise a removable re-attachable seal 28 or partially affixed seal 29. Refer to FIG. 2 and the description above for a drawing and discussion of the removable re-attachable seal. Refer to FIG. 3 and the description above for a drawing and discussion of the partially affixed seal. The top wall of the condom compartment 21 also comprises a raised annular ring 26. The raised annular ring 26 is positioned between the protruding curved edge of the top wall of the compartment 22 and the removable seal 25. The raised annular ring 26 provides a barrier to the migration of liquid material contained in an open condom compartment 20 when the container 110 is seated in a device used to heat its contents. The raised annular ring 26 helps prevent liquid material from entering the part of a device that heats the contents of the compartments 20, 130, 150.

In lieu of a single personal lubricant compartment 30, two congruent personal lubricant compartments contain personal lubricant or sexually stimulating lubricant hereinafter referred to as PLC-A 130 and PLC-B 150. PLC-A 130 and PLC-B 150 are positioned on opposing ends of the container 110 removably adjoined to the condom compartment 20 at a protruding curved edge of the top wall of each compartment 22, 132, 152. Inasmuch as PLC-A 130 and PLC-B 150 are congruent, only PLC-A 130 is described further.

PLC-A 130 is in the shape of a funnel 40. The protruding curved edge of the top wall of PLC-A 132, two side walls 134 (top edge only shown) separated by a discharge element 43, and the discharge element 43 mark the perimeter of the top of PLC-A 130. The top wall of PLC-A 131 is tapered sloping downward away from a curved interior side wall 135, the broad end of the funnel 41, and terminating at the discharge element 43, the narrow end of the funnel 42, therefore; the broader end 41 is higher than the narrower end of the funnel 42. The downward slope facilitates the flow of personal lubricant and, concomitantly, the emptying of PLC-A 130. Personal lubricant discharged is, for the most part, gravity fed. The narrow end of the funnel 42 comprises an open-ended discharge element 43 or fitting designed to receive a removable dispenser. Before discharging the contents, a protective seal 45 (shown by a dashed line) within the discharge element 43 is ruptured presumably by a piercing element of the removable dispenser. The discharge element 43 may also comprise a cap 44 that must be removed from the end of the element 43 before rupturing the protective seal 45.

Figure 8:
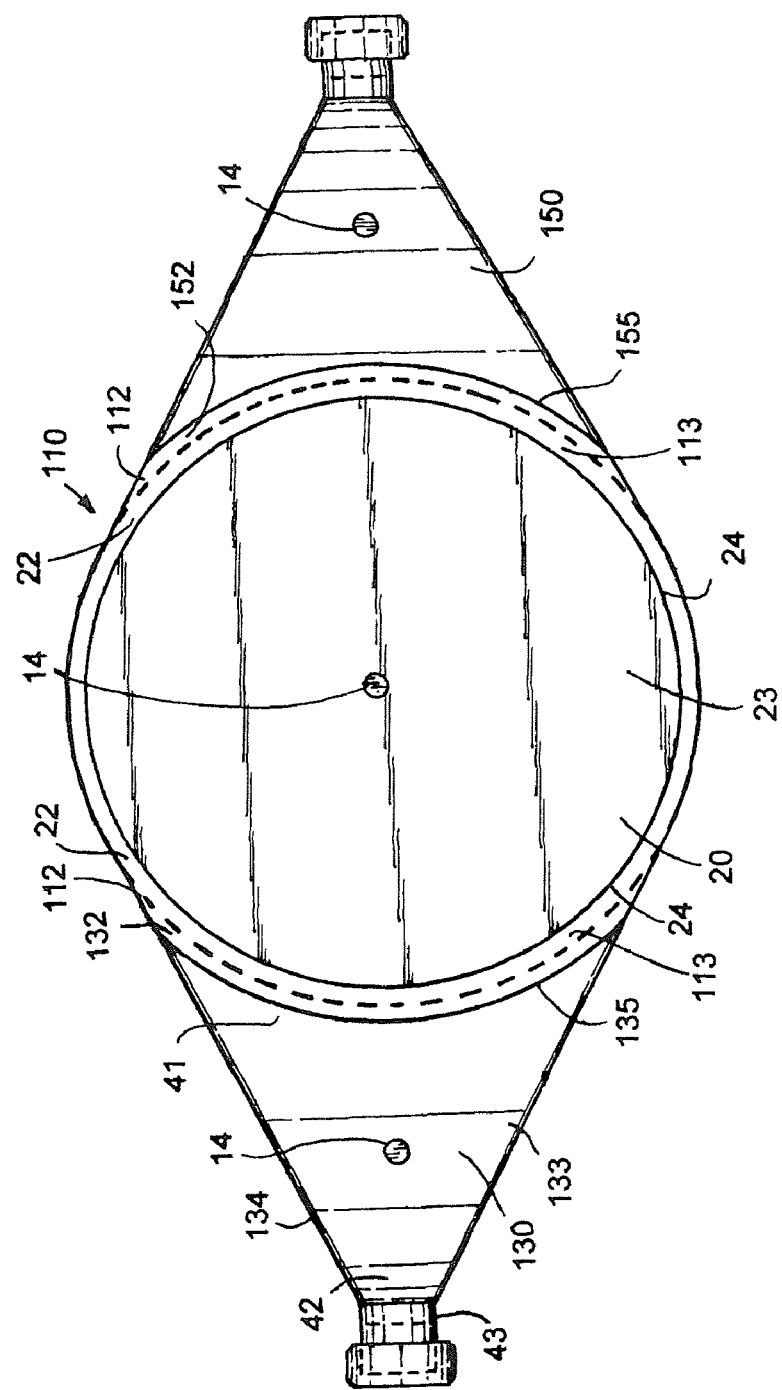
FIG. 8 shows a bottom view of a second embodiment of a combination condom and personal lubricant container.

FIG. 8 shows a bottom view of the second embodiment of the combination condom and personal lubricant container 110. The perforations in the top of the container 112 and the curved edge of the top wall of each compartment 22, 132, 152 are in view.

The condom compartment 20 is positioned at or near the center of the container 110. A bottom wall of the condom compartment 23 is substantially flat. A cylindrical wall 24 (bottom edge only shown) marks the perimeter of the bottom wall of the compartment 23 and faces a curved interior wall of each congruent compartment 135, 155 (bottom edge only shown). The bottom wall of the compartment 23 may comprise a temperature sensing aid 14. The temperature sensing aid 14 allows the temperature of the contents enclosed within the compartment 20 to be monitored when the contents of the compartment 20 are heated by a device in which the container 110 is seated. The temperature sensing aid 14 may be a temperature sensor known in the art or a component known in the art that makes contact with a temperature sensor a part of the heating apparatus.

PLC-A 130 is positioned at an end of the container 110 flanking the condom compartment 20. The curved interior wall 135 (bottom edge only shown), two side walls 134 (bottom edge only shown) separated by a discharge element 43, and the discharge element 43 mark the perimeter of the bottom of PLC-A 130. The curved interior wall of PLC-A 135 faces the cylindrical wall of the condom compartment 24. The bottom wall of the compartment 133 is tapered and horizontally positioned in the container 110 and extends away from the bottom horizontal edge of the curved interior wall 135, the broad end of the funnel 41, toward the discharge element 43, the narrow end of the funnel 42. The bottom wall of the compartment 133 may comprise a temperature sensing aid 14. The temperature sensing aid 14 allows the temperature of the contents enclosed within PLC-A 130 to be monitored when the contents of PLC-A 130 are heated by a device in which the container 110 is seated. The temperature sensing aid 14 may be a temperature sensor known in the art or a component known in the art that makes contact with a temperature sensor a part of the heating device. The drawing discloses two curved spaces 113 between the cylindrical wall of the condom compartment 24 and a curved interior wall of each congruent compartment 135, 155 which may accommodate a heating element of the device.

Figure 9:
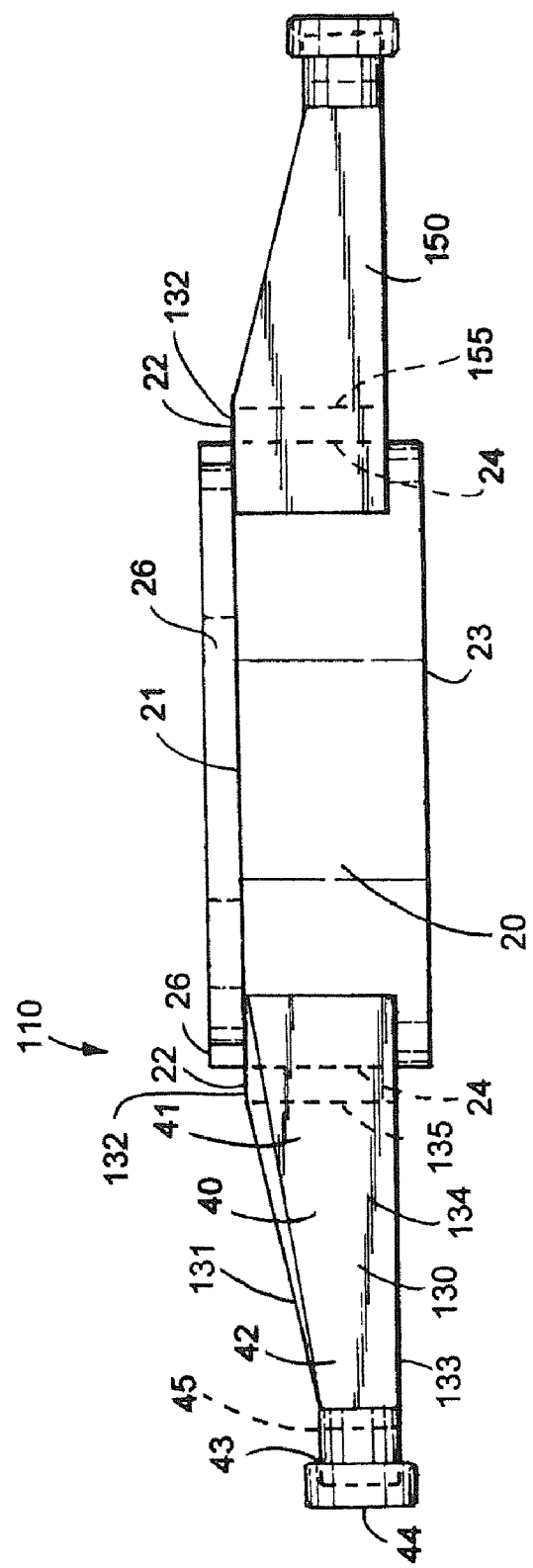
FIG. 9 shows a side view of a second embodiment of a combination condom and personal lubricant container.

FIG. 9 shows a side view of the second embodiment of the combination condom and personal lubricant container 110. The drawing favors the length of the container 110.

The condom compartment 20 is positioned at the distal end of the container 110. The condom compartment 20 comprises a substantially flat top wall 21 (edge only shown) and bottom wall 23 (edge only shown) substantially parallel to one another and a cylindrical wall 24 substantially perpendicular to the top wall 21 and bottom wall 23 hermetically sealed to form an airtight enclosure in which the contents reside. The top wall 21 comprises a protruding curved edge 22. The cylindrical wall 24 faces the curved interior wall of the personal lubricant compartment 35. Preferably, the raised annular ring 26 is positioned on the top wall of the condom compartment 21. The cylinder shaped condom compartment 20 is deep enough to accommodate one or more condoms and a personal lubricant or sexually stimulating lubricant in which said one or more condoms are immersed.

The personal lubricant compartment 130 is positioned at the proximal end of the container 10. The compartment 130 is in the shape of a funnel 40. The compartment comprises a sloping top wall 131, a horizontally positioned bottom wall 133 (side edge only shown), two tapered side walls 134 (only one wall shown), and the discharge element 43, the taper terminus for said walls. The compartment 130 also comprises a curved interior wall 135 marking the broad end of the funnel 41. The curved interior side wall 135 is joined to the top wall 131, bottom wall 133, and each side wall 134 at its top horizontal edge, bottom horizontal edge, and vertical edge, respectively. Said walls and discharge element 43 are hermetically sealed to form an airtight enclosure in which the contents reside. The top wall of the compartment 131 slopes downward diagonally away from the top horizontal edge of the curved interior side wall 135, the broad end of the funnel 41, toward the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 130. Personal lubricant discharged is, for the most part, gravity fed. The narrow end of the funnel 42 comprises an open-ended discharge element 43 or fitting designed to receive a removable dispenser. Before discharging the contents, a protective seal 45 within the discharge element 43 is ruptured presumably with a piercing element of the removable dispenser. The discharge element 43 may also comprise a cap 44 that must be removed from the end of the element 43 before rupturing the protective seal 45.

Figure 10:
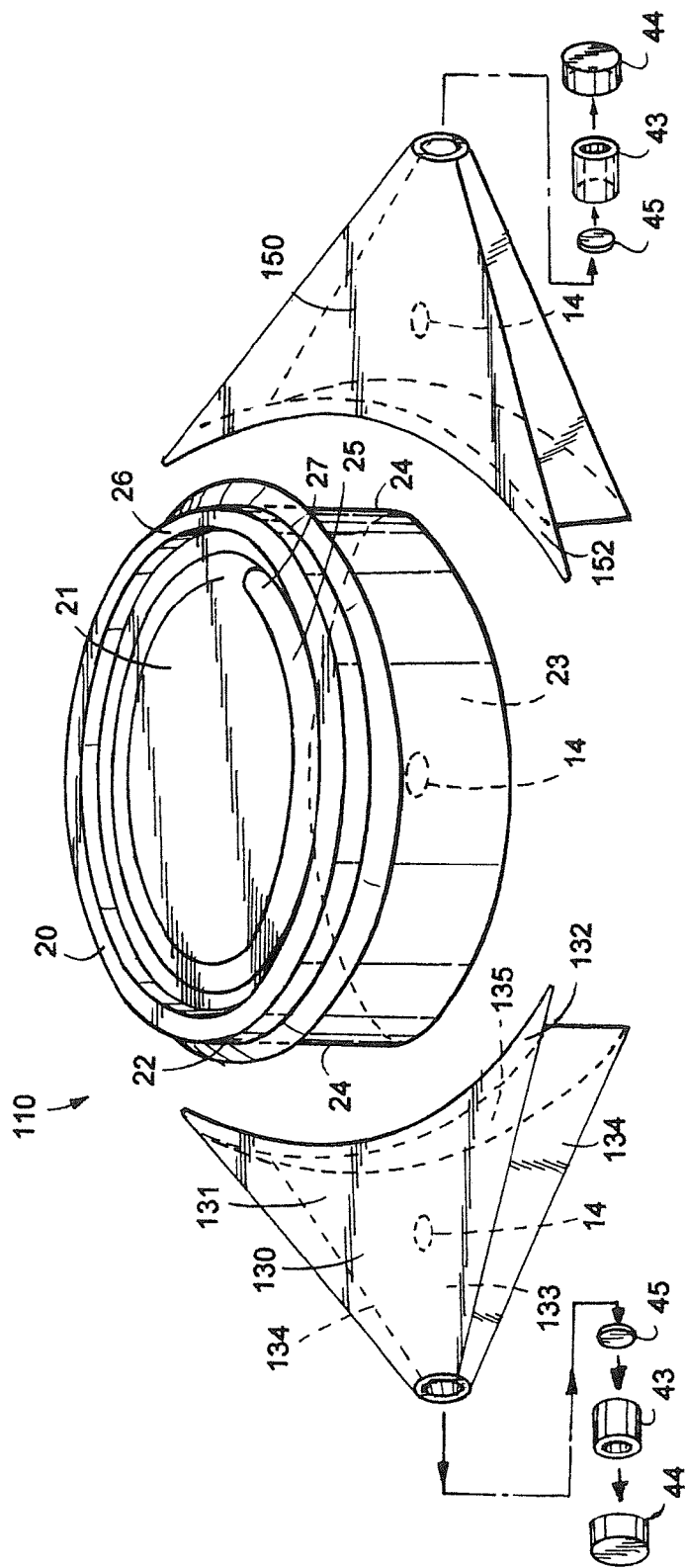
FIG. 10 shows an exploded view of a second embodiment of a combination condom and personal lubricant container.

FIG. 10 shows an exploded view of the second embodiment of the combination condom and personal lubricant container 110. The condom compartment 20 and the congruent personal lubricant compartments 130, 150 are separated from another with the aid of perforations in the container 112. The condom compartment 20 is shown to comprise a top wall 21 comprising a removable seal 25 in the shape of an annular strip with a tab 27, a protruding curved edge 22 and a raised annular ring 26 positioned between the seal 25 and the protruding curved edge 22 and a cylindrical wall 24. A bottom wall 23 is hidden but the temperature sensing aid 14 comprising the bottom wall 23 is shown by a dashed oval. In lieu of a removable seal 25, the top wall of the compartment may comprise a removable reattachable seal 28 (not shown) or a partially affixed seal 29 (not shown). Although the drawing depicts the top wall 21 comprising the raised annular ring 26 and the hidden bottom wall comprising a temperature sensing aid 14, these elements are only preferred. Each congruent personal lubricant compartment 130, 150 is shown to comprise a discharge element 43 which is separated from the compartment 130 at the narrow end of the funnel 42. A cap 44 and protective seal 45 are separated from the discharge element 43. The discharge element 43 is open-ended fitting shown to be cylindrical in shape. The three dimensional shape of the condom compartment 20 and the congruent personal lubricant compartments 130, 150 defines the volume of the contents contained therein.

Third Embodiment of a Combination Condom and Personal Lubricant Container—FIGS. 11, 12, 13, 14

FIGS. 11-14 shows various views of an article of manufacture comprising a condom compartment 220 removably adjoined to a personal lubricant compartments 230 hereinafter referred to as a combination condom and personal lubricant container 210. The container 210 is in the shape of a pentagon. The container 210 is disposable. The compartments 220, 230 comprising the container 210 are constructed of a flexible, semi-rigid, or rigid packaging material 11 comprising properties that conduct heat such as aluminum. The condom compartment 220 is removably adjoined to a personal lubricant compartments 230 at a protruding straight edge of the top wall of each compartment 222, 232 forming a common border. The compartments 220, 230 may be detached from one another with the aid of perforations in the top of the container 212 arranged in a straight pattern along the common border.

Figure 11:
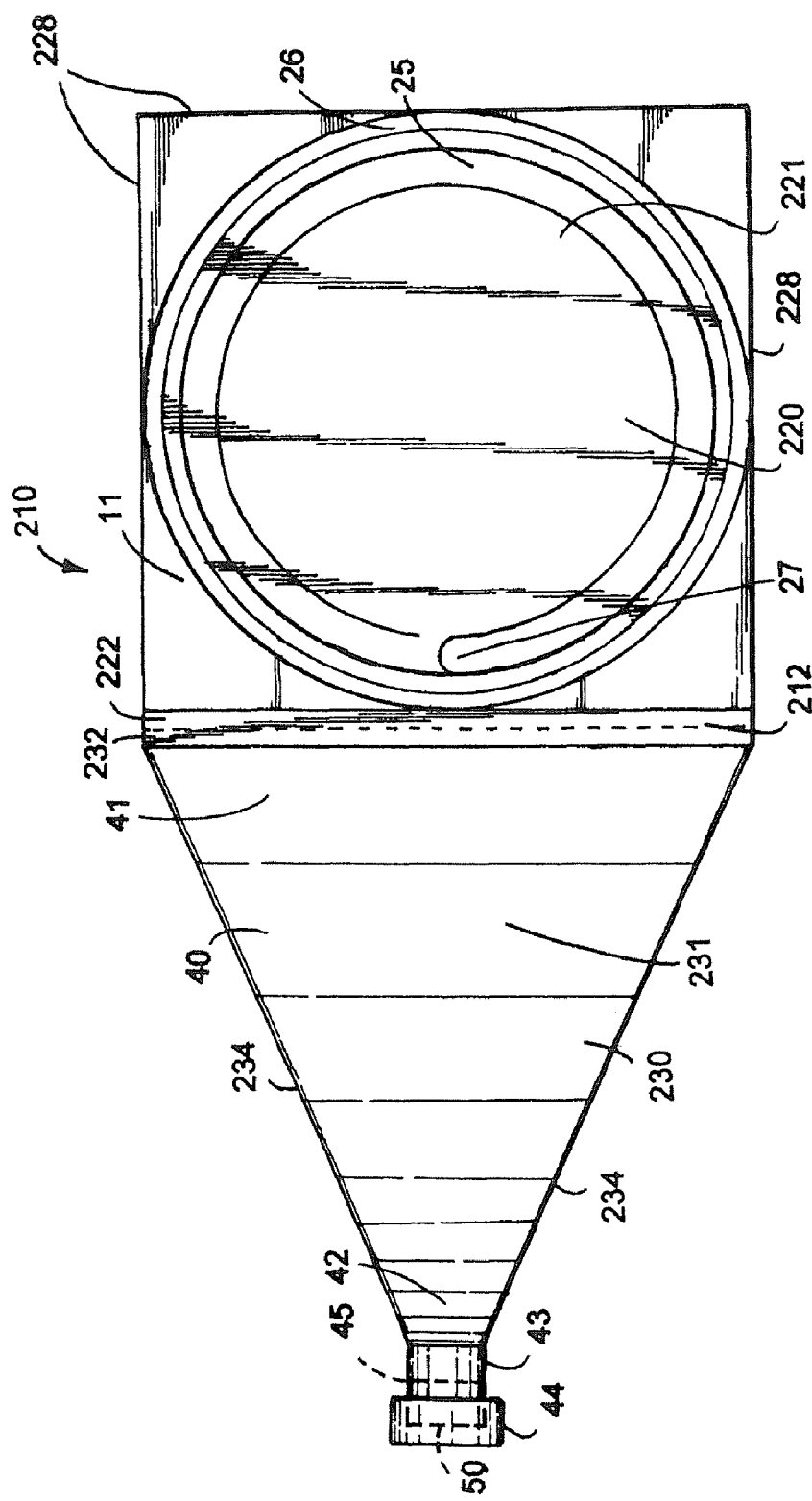
FIG. 11 shows a top view of a third embodiment of a combination condom and personal lubricant container.

FIG. 11 shows a top view of a third embodiment of the combination condom and personal lubricant container 210. The condom compartment 220 is positioned at the distal end (in relation to the point of discharge 50 of the contents in the personal lubricant compartment 230) of the container 210. The top view shows the top wall of the condom compartment 221 to be rectangular in shape. The top wall 221 comprises a removable seal 25. The drawing depicts a removable seal 25 in the shape of an annular strip with a tab 27. By pulling the tab 27 and removing the seal 25, the contents are accessed and may be manually removed. The seal 25 may not be reattached. The top wall of the condom compartment 221 may comprise a removable re-attachable seal 28 or partially affixed seal 29 in lieu of a removable seal 25. Refer to FIG. 2 and the description above for a drawing and discussion of the removable re-attachable seal. Refer to FIG. 3 and the description above for a drawing and discussion of the partially affixed seal. The top wall of the condom compartment 221 also comprises a protruding straight edge 222 extending out from a rectangular side wall 229. Three rectangular side walls 228 (top edge only shown) and the protruding straight edge of the top wall of the compartment 222 mark the perimeter of the top wall of the compartment 221. Preferably, the top wall of the condom compartment 221 also comprises a raised annular ring 26. The raised annular ring 26 is positioned between the perimeter of the top wall of the compartment 221 and the removable seal 25. The raised annular ring 26 provides a barrier to the migration of liquid material contained in an open condom compartment 220 when the container 210 is seated in a device used to heat its contents. The raised annular ring 26 helps prevent liquid material from entering the part of a device that heats the contents of the compartments 220, 230.

The proximal end of the container 210 comprises a personal lubricant compartment 230. The personal lubricant compartment 230 is in the shape of a funnel 40. The top wall of the personal lubricant compartment 231 comprises a protruding straight edge 232 extending away from a rectangular side wall 235 (shown by a dashed line). The protruding straight edge 232, two side walls 234 (top edge only shown)

separated by a discharge element 43 and the discharge element 43 mark the perimeter of the top of the personal lubricant compartment 230. The top wall of the compartment 231 is tapered sloping downward from the rectangular side wall 232, the broad end of the funnel 41, and terminating at the discharge element 43, the narrow end of the funnel, therefore, the broader end 41 is higher than the narrower end of the funnel 42. The downward slope facilitates the flow of personal lubricant and, concomitantly, the emptying of the personal lubricant compartment 230. Personal lubricant discharged is, for the most part, gravity fed. The narrow end of the funnel 42 comprises an open-ended discharge element 43 or fitting designed to receive a removable dispenser. Before discharging the contents, a protective seal 45 (shown by a dashed line) within the discharge element 43 is ruptured presumably with a piercing element of a removable dispenser. The discharge element 43 may also comprise a cap 44 that must be removed from the end of the element 43 before rupturing the protective seal 45.

Figure 12:
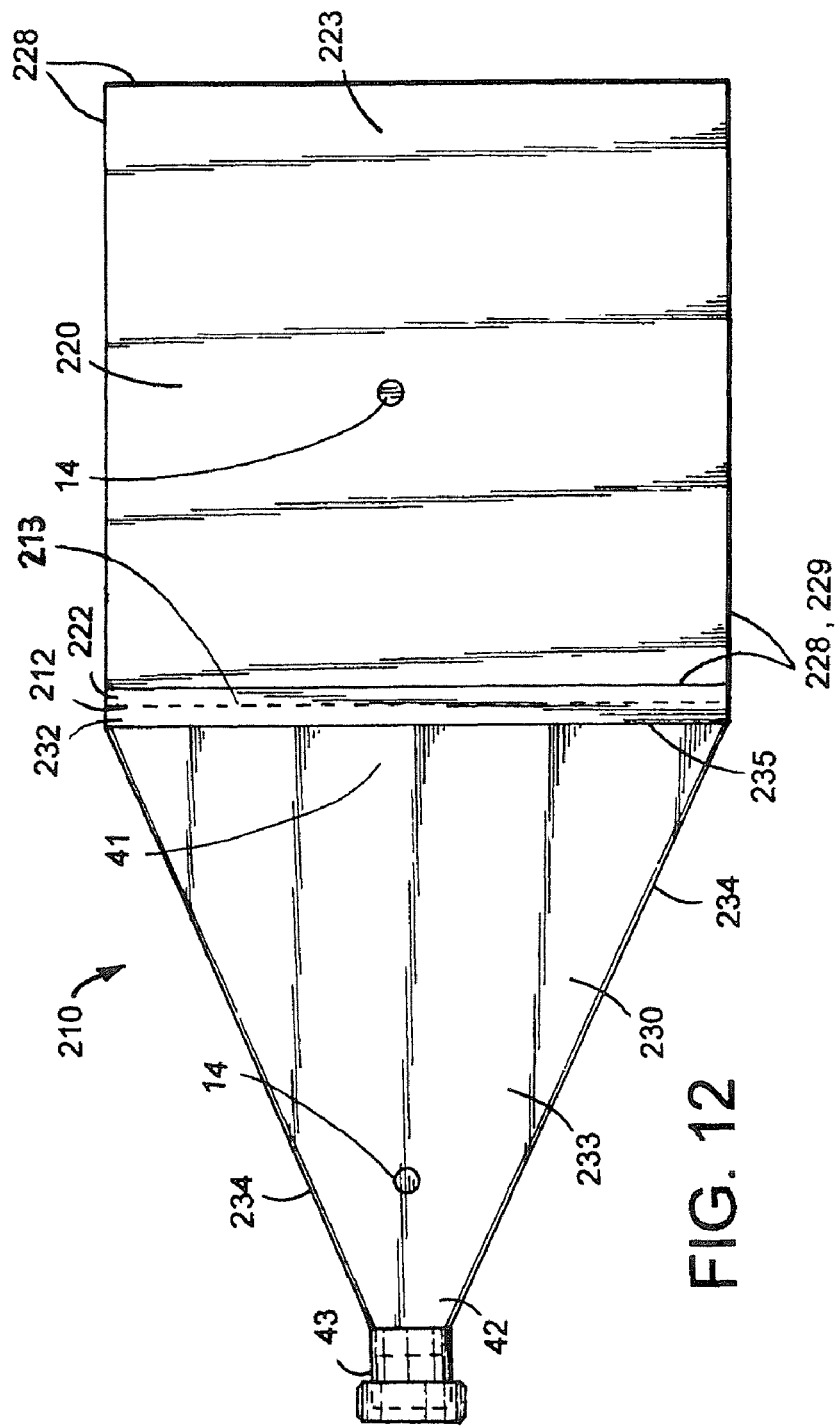
FIG. 12 shows a bottom view of a third embodiment of a combination condom and personal lubricant container.

FIG. 12 shows a bottom view of the third embodiment of the combination condom and personal lubricant container 210. The perforations in the top of the container 212 and the protruding straight edge of the top wall of each compartment 222, 232 are in view.

The distal end of the container 210 comprises the condom compartment 220. The bottom wall of the compartment 223 is substantially flat and rectangular in design. Four rectangular side walls 228 (bottom edge only shown) located about the condom compartment 220 mark the perimeter of the bottom wall of the compartment 223. A rectangular interior side wall 229 (bottom edge only shown) faces a rectangular interior side wall of the personal lubricant compartment 235 (bottom edge only shown) each wall substantially equal in length and equidistant from one another. The bottom wall of the compartment 223 may comprise a temperature sensing aid 14. The temperature sensing aid 14 allows the temperature of the contents enclosed within the compartment 220 to be monitored when the contents of the compartment 220 are heated by a device in which the container 210 is seated. The temperature sensing aid 14 may be a temperature sensor known in the art or a component known in the art that makes contact with a temperature sensor a part of the heating device.

The proximal end of the container 210 comprises the personal lubricant compartment 230. The bottom wall of the compartment 233 is triangular in shape. A rectangular interior side wall 235 (bottom edge only shown), two side walls 234 (bottom edge only shown) separated by the discharge element 43, and the discharge element 43 mark the perimeter of the bottom of the compartment 230. The rectangular interior side wall 235 faces the rectangular interior side wall of the condom compartment 229 said walls substantially equal in length and equidistant from one another. The bottom wall of the compartment 233 is tapered and horizontally positioned in the container 210 and extends away from the bottom horizontal edge of the rectangular side wall 235, the broad end of the funnel 41, toward the discharge element 43, the narrow end of the funnel 42. The bottom wall of the compartment 233 may comprise a temperature sensing aid 14. The temperature sensing aid 14 allows the temperature of the contents enclosed within the compartment 230 to be monitored when the contents of the compartment 230 are heated by a device in which the container 210 is seated. The temperature sensing aid 14 may be a temperature sensor known in the art or a component known in the art that makes contact with a temperature sensor a part of the heating device. The drawing discloses a straight space 213 between the opposing interior rectangular side walls of the condom compartment 229 and the personal lubricant compartment 235 which may accommodate a heating element of the device.

Figure 13:
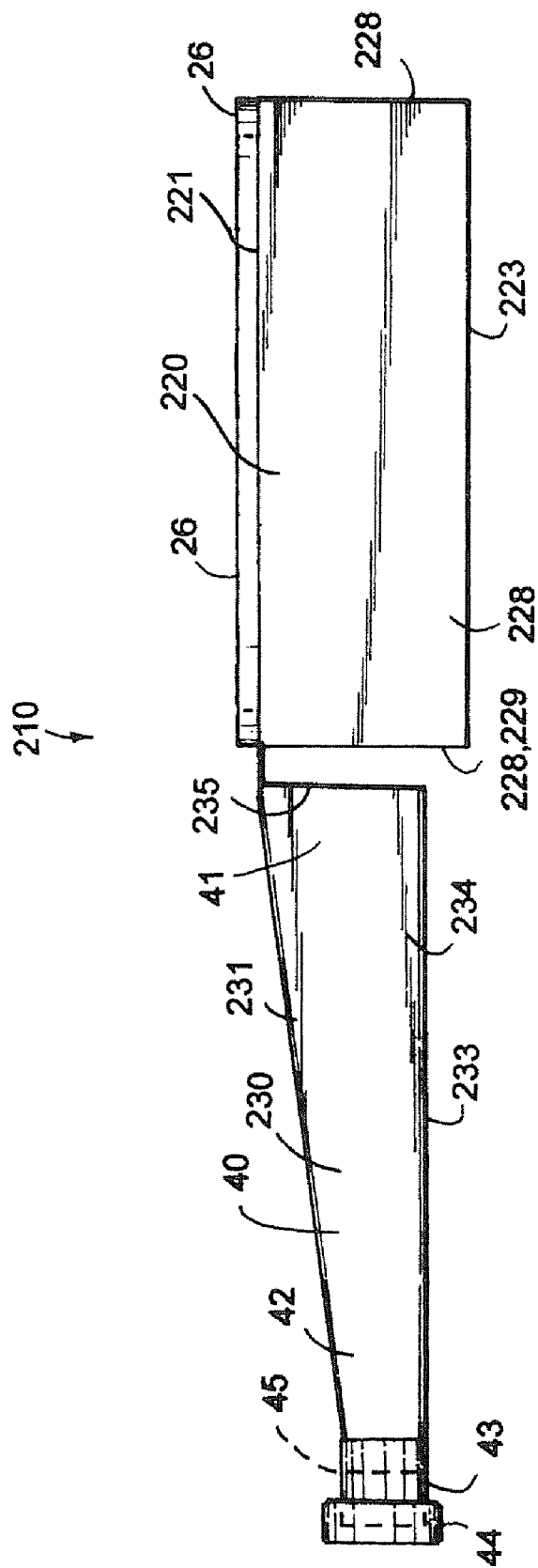
FIG. 13 shows a side view of a third embodiment of a combination condom and personal lubricant container.

FIG. 13 shows a side view of the third embodiment of the combination condom and personal lubricant container 210. The drawing favors the length of the container 210.

The distal end of the container 210 comprises the condom compartment 220. The condom compartment 220 is in the shape of a rectangular box. The walls comprising the condom compartment 220 are hermetically sealed to form an airtight enclosure in which the contents reside. The drawing shows the side of a rectangular side wall 228 comprising a substantially flat top wall 221 (top edge only shown) and bottom wall 223 (bottom edge only shown) and two rectangular side walls 228 (side edge only shown). One of the rectangular side walls 228 is a rectangular interior side wall 229 facing a rectangular interior side wall of the personal lubricant compartment 235. The raised annular ring 26 is positioned on the top wall of the condom compartment 221. The condom compartment 220 is deep enough to accommodate one or more condoms and a personal lubricant or sexually stimulating lubricant in which said one or more condoms are immersed.

The proximal end of the container 210 comprises the personal lubricant compartment 230. The personal lubricant compartment 230 is in the shape of a funnel 40. The compartment comprises a sloping top wall 231, a horizontally positioned bottom wall 233 (side edge only shown), two tapered side walls 234 (only one wall shown), and the discharge element 43, the taper terminus for said walls. The compartment 230 also comprises a rectangular interior side wall 235 marking the broad end of the funnel 41. The rectangular interior side wall 235 is joined to the top wall 231, bottom wall 233, and each side wall 234 at its top horizontal edge, bottom horizontal edge, and vertical edge, respectively. Said walls and discharge element 43 are hermetically sealed to form an airtight enclosure in which the contents reside. The top wall of the compartment 231 slopes downward diagonally away from the top horizontal edge of the rectangular interior side wall 235, the broad end of the funnel 41, toward the discharge element 43, the narrow end of the funnel 42, therefore; the broader end 41 is higher than the narrower end of the funnel 42. The downward slope facilitates the flow of personal lubricant and, concomitantly, the emptying of the personal lubricant compartment 230. Personal lubricant discharged is, for the most part, gravity fed. The narrow end of the funnel 42 comprises an open-ended discharge element 43 or fitting designed to receive a removable dispenser. Before discharging the contents, a protective seal 45 within the discharge element 43 is ruptured presumably with a piercing element of the removable dispenser. The discharge element 43 may also comprise a cap 44 that must be removed from the end of the element 43 before rupturing the protective seal 45.

Figure 14:
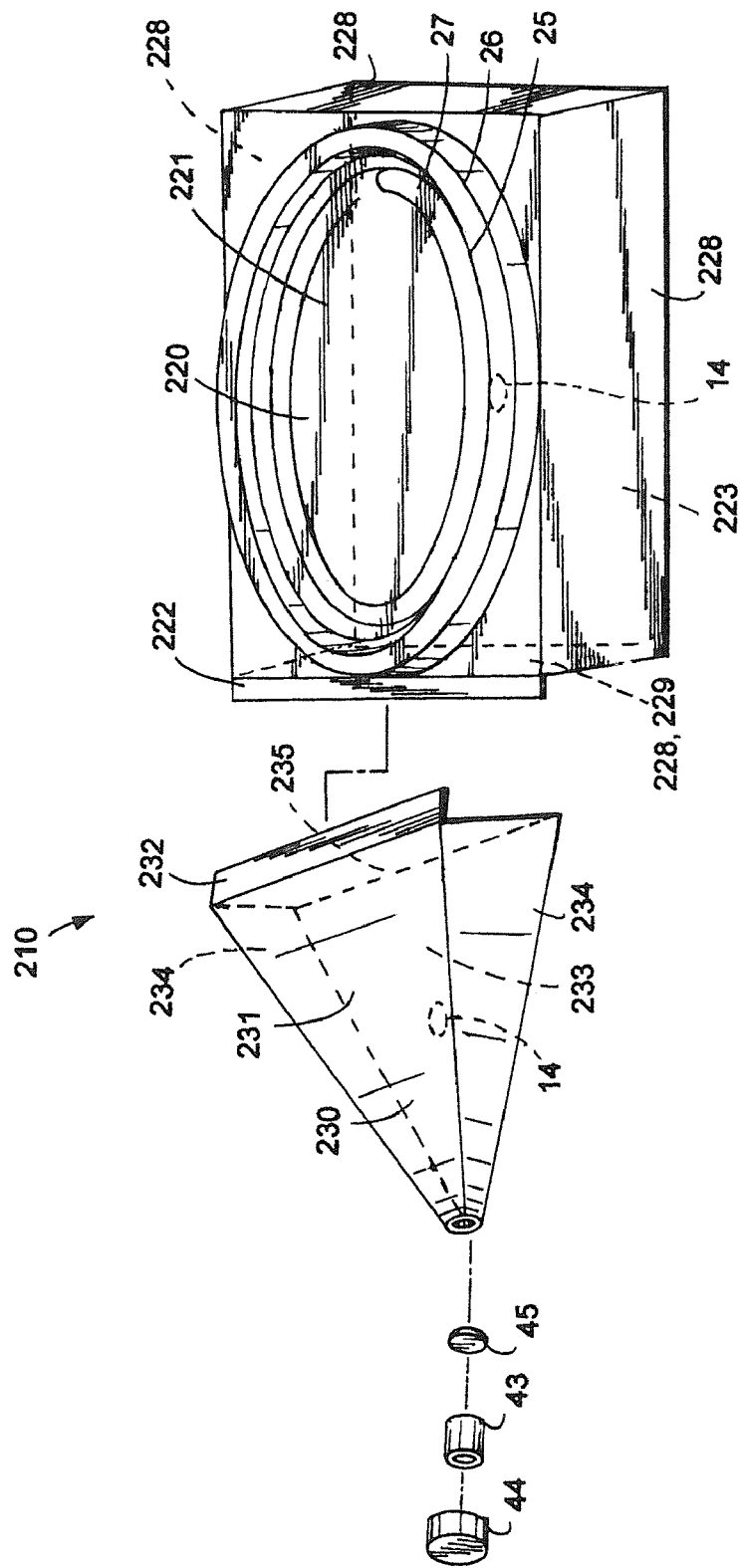
FIG. 14 shows an exploded view of a third embodiment of a combination condom and personal lubricant container.

FIG. 14 shows an exploded view of the third embodiment of the combination condom and personal lubricant container 210. The condom compartment 220 and personal lubricant compartment 230 are separated from one another with the aid of perforations in the container 212. The rectangular shaped condom compartment 220 is shown to comprise a top wall 221 comprising a removable seal 25 in the shape of an annular strip with a tab 27, a protruding straight edge 222 and a raised annular ring 26 positioned between the seal 25 and the protruding straight edge 222 and rectangular side walls 228. A rectangular side wall 228 and the bottom wall 23 are hidden; however, the temperature sensing aid 14 comprising the bottom wall 223 is shown by a dashed oval. In lieu of a removable seal 25, the top wall of the compartment may comprise a removable re-attachable seal 28 (not shown) or a partially affixed seal 29 (not shown). Although the drawing depicts the top wall 221 comprising the raised annular ring 26 and the hidden bottom wall 223 comprising a temperature sensing aid 14, these elements are only preferred. The personal lubricant compartment 230 is shown to comprise a discharge element 43 which is separated from the compartment 230 at the narrow end of the funnel 42. A cap 44 and protective seal 45 are separated from the discharge element 43. The discharge element 43 is an open-ended fitting shown to be cylindrical in shape. The three dimensional shape of the condom compartment 20 and personal lubricant compartment 30 defines the volume of the contents contained therein.

Operation—First, Second and Third Embodiments of a Combination Condom and Personal Lubricant Container 1. Assembling the combination condom and personal lubricant container.

The first, second and third embodiments of the combination condom and personal lubricant container 10, 110, 210 comes assembled. The container 10, 110, 210 comprises a compartment 20, 220 enclosing one or more condoms and a personal lubricant or sexually stimulating lubricant in which said one or more condoms are immersed and a personal lubricant compartment 30, 130, 230 enclosing a personal lubricant. Alternatively, the personal lubricant compartment 30, 130, 230 may enclose sexually stimulating lubricant. The contents of the compartments are used in sexual activities.

The condom is preferably a male condom known in the art that is sold over the counter under various brand names. Personal lubricant includes a lubricant sold over the counter under various brand names including KY, Durex, Astroglide, and Liquid Silk and is not limited to water-based lubricants.

2. Removing or discharging the contents of the combination condom and personal lubricant container.

The first, second and third embodiments of the combination condom and personal lubricant container 10, 110, 210 comprise a condom compartment and at least one personal lubricant compartment each compartment comprising the means to access and remove or dispense the contents.

The top wall of the condom compartment 21, 221 comprises one of the following seals; a removable seal 25 in the shape of an annular strip with a tab 27, a removable reattachable seal 28 with a tab 27 or a partially affixed seal 29 with a tab 27. By pulling the tab 27 and removing or opening the seal 25, 28, 29, the contents of the compartment 20, 220 are accessed and may be removed manually. The removable seal 25 is not re-attachable to the top wall of the compartment 21, 221. The removable re-attachable seal 28 may be reattached to the top wall 21, 221 by pressing the seal against the circular support for a reattachable seal 281. By re-attaching the seal 28, the remaining contents of the compartment 20, 220 are hygienically secured avoiding spillage. The underside of a re-attachable seal 28 and top of a circular support for a re-attachable seal 281 comprise an adhesive to secure one to the other; however, other securing means known in the art may be used. The partially affixed seal 29 is opened and closed without removing the seal 29 from the top wall 21, 221. The seal 29 may be closed by pressing the seal 29 against the circular support for a partially affixed seal 291. By closing the seal 29, the remaining contents of the compartment 20 are hygienically secured avoiding spillage. The underside of a partially affixed seal 29 and top of a circular support for a partially affixed seal 291 comprise an adhesive to secure one to the other; however, other securing means known in the art may be used.

The contents of the personal lubricant compartment 30, 130, 230 are discharged by activating a removable dispenser. The personal lubrication compartment 30, 130, 230 comprises a funnel 40 which comprises an open-ended discharge element 43 or fitting attached to the narrow end of the funnel 42 designed to receive a removable dispenser. Before discharging personal lubricant, a protective seal 45 within the discharge element 43 is ruptured presumably with a piercing element of the dispenser. The discharge element 43 may also comprise a cap 44 that must be removed from the end of the element 43 before rupturing the protective seal 45. The dispenser may be a component of a device used to heat the contents of the compartment 30, 230.

3. Heating the contents of the combination condom and personal lubricant container.

The first, second and third embodiments of the combination condom and personal lubricant container 10, 110, 210 comprise a condom compartment and at least one personal lubricant compartment each compartment constructed of a flexible, semi-rigid, or rigid packaging material comprised of properties that conduct heat 11. The container 10, 110, 210 may be seated in a warming device for the purpose of heating the contents of the compartments to a desired temperature prior to removal or discharge. A condom is warmed as a result of being immersed in the liquid material that is itself warmed when the condom compartment 20, 220 is heated by a warming device. Each compartment may comprise a temperature sensing aid 14 allowing the temperature of the contents to be monitored when heated by a device in which the container 10, 110, 210 is seated. The temperature sensing aid 14 may be a temperature sensor known in the art or a component known in the art that makes contact with a temperature sensor a part of the heating device.

Figure 15:
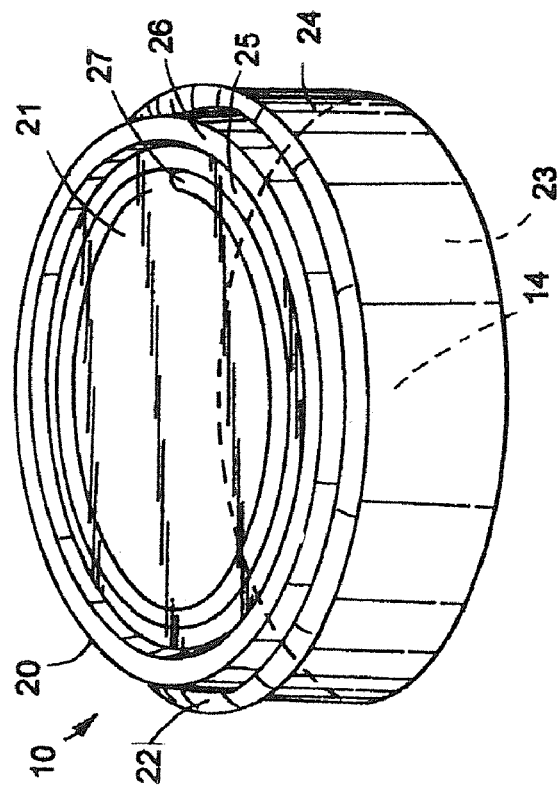
FIG. 15 shows a perspective view of a first embodiment of a combination condom compartment and personal lubricant compartment kit.
Figure 15:
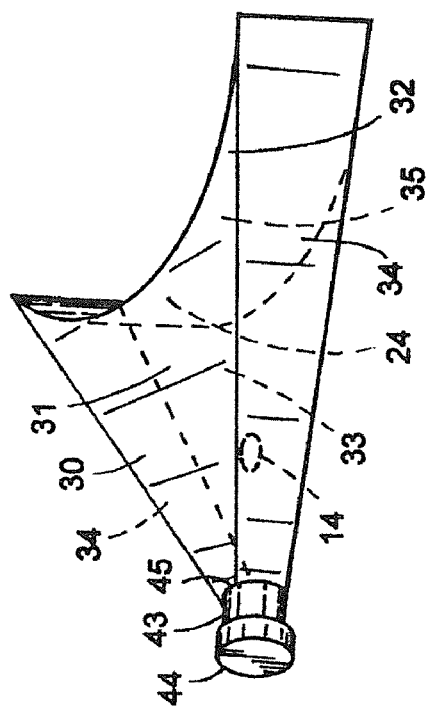

First Embodiment of a Combination Condom Compartment and Personal Lubricant Compartment Kit—FIG. 15

FIG. 15 shows a perspective view of a first embodiment of a combination condom compartment and personal lubricant compartment kit 310. The kit 310 comprises at least one condom compartment 20 wherein said at least one condom compartment 20 is associated with at least one personal lubricant compartment 30. The elements of the kit 310, at least one condom compartment 20 and at least one personal lubricant compartment 30, are combined but not attached. The elements may come in a package, box, or other container (not shown).

Figure 16:
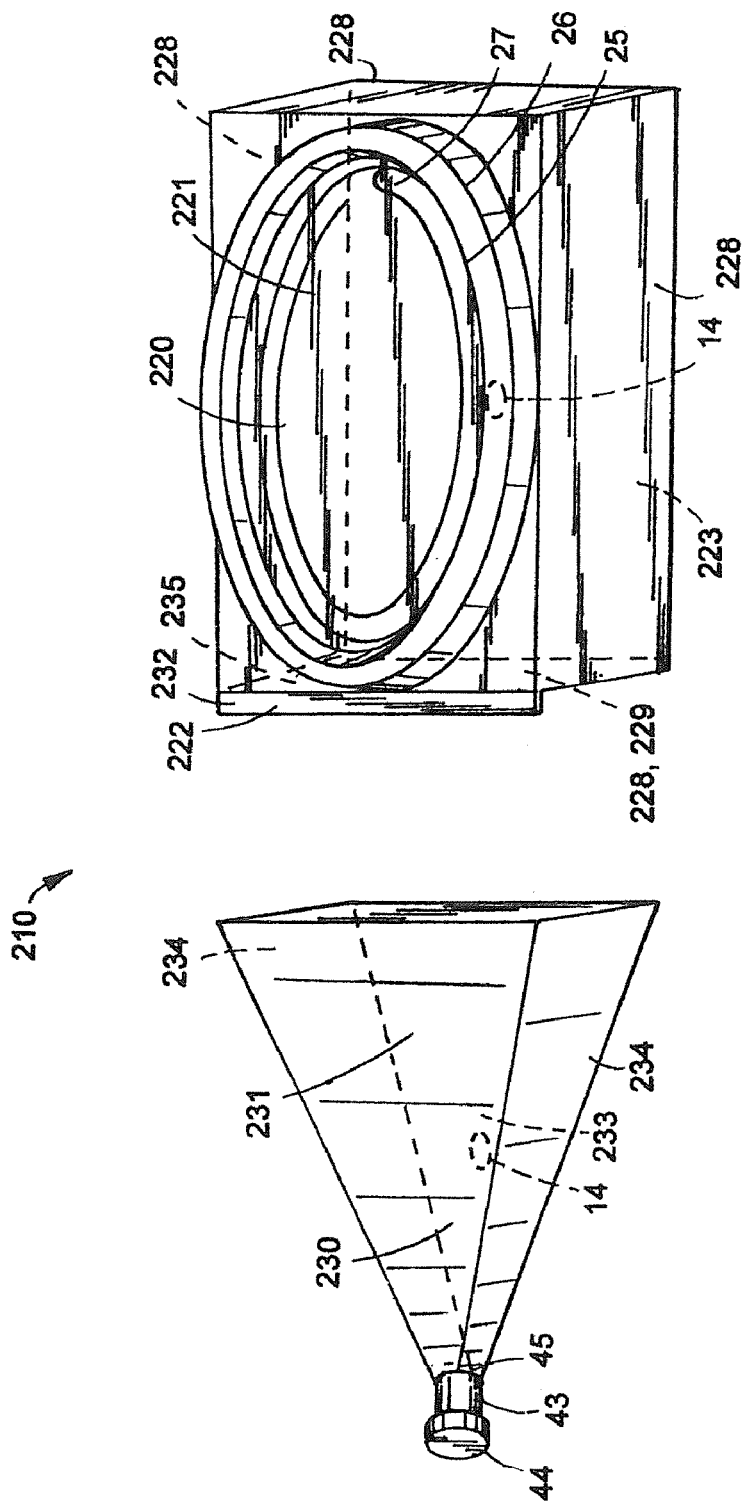
FIG. 16 shows a perspective view of a second embodiment of a combination condom compartment and personal lubricant compartment kit.

First Embodiment of a Combination Condom Compartment and Personal Lubricant Compartment Kit—FIG. 16

FIG. 16 shows a perspective view of a second embodiment of a combination condom compartment and personal lubricant compartment kit 410. The kit 410 comprises at least one condom compartment 220 wherein said at least one condom compartment 220 is associated with at least one personal lubricant compartment 230. The elements of the kit 410, at least one condom compartment 220 and at least one personal lubricant compartment 230, are combined but not attached. The elements may come in a package, box or other container (not shown).

Operation—First and Second Embodiments of the Combination Condom Compartment and Personal Lubricant Compartment Kit 1. Assembling the combination condom and personal lubricant kit.

Preferably, the first and second embodiments of the combination condom compartment and personal lubricant compartment kit 310, 410 may come in a package, box or other container. The contents of the compartments 20, 30, 220, 230 comprising the kits are used in sexual activities.

The condom compartment 20, 220 encloses one or more condoms and a personal lubricant or sexually stimulating lubricant in which said one or more condoms are immersed. The condom is preferably a male condom known in the art. The personal lubricant compartment 30, 230 contains personal lubricant or, alternatively, sexually stimulating lubricant. Personal lubricant includes a lubricant sold under the brand name KY, Durex, Astroglide, Liquid Silk, among others, and is not limited to water-based lubricants.

2. Removing or discharging the contents of the condom and personal lubricant comprising the kit.

Refer to the description above regarding a discussion about removing the contents from the condom compartment. Refer to the description above regarding a discussion about discharging the contents from the personal lubricant compartment.

3. Heating the contents of the condom compartment and personal lubricant compartment comprising the kit.

Refer to the description above regarding a discussion about heating the contents of the condom compartment prior to removal and use. Refer to paragraph 0084 above regarding a discussion about heating the contents of the personal lubricant compartment prior to discharge and use.

Figure 17:
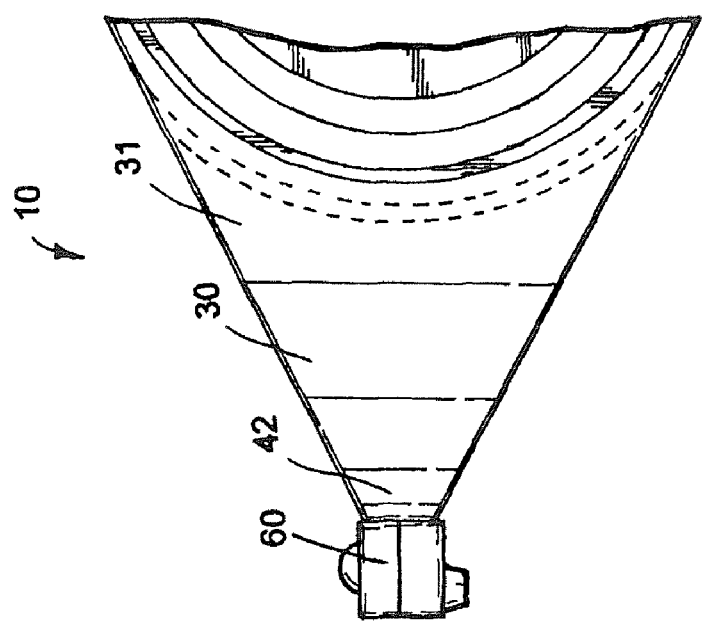
FIG. 17 shows a perspective view of a personal lubricant compartment comprising a permanently attached dispenser.

Alternate Embodiment of a Personal Lubricant Compartment Comprising a Permanently Dispenser—FIG. 17

FIG. 17 shows a perspective view of a personal lubricant compartment 30 comprising a permanently attached dispenser 60. The drawing favors the top wall of the personal lubricant compartment 31 and the portion of the compartment 30 comprising the funnel 40. The narrow end of the funnel 42 comprises a permanently attached dispenser 60. The permanently attached dispenser is one known in the art.

The other embodiments of a personal lubricant compartment 130, 230 may also comprise a permanently attached dispenser 60.

Operation—Alternate Embodiment—Permanently Attached Dispenser

1. Assembling of the permanently attached dispenser onto the personal lubricant compartment.

The alternate embodiment of the personal lubricant compartment 30 comes assembled.

2. Removing or discharging the contents of the personal lubricant compartment.

The contents of a personal lubricant compartment 30 are discharged by activating the permanently attached dispenser 60.

Advantages of the Embodiments of the Invention

From the descriptions above, a number of advantages of the various embodiments of the invention over prior art become apparent. Reference numbers used are those set forth in the description of the first embodiment of the combination condom and personal lubricant container 10 unless otherwise stated.

The combination condom and personal lubricant container 10 comprises a condom compartment 20 in which is enclosed one or more condoms and a personal lubricant or sexually stimulating lubricant in which said one or more condoms are immersed, and at least one personal lubricant compartment 30 in which is enclosed a personal lubricant or, alternatively, a sexually stimulating lubricant. The compartments are constructed of a packaging material comprising properties that conduct heat such as aluminum. The container 10 or a compartment 20, 30 is placed in a device where the contents of the compartments are heated prior to their removal or discharge. The contents enclosed in a compartment may be heated to a temperature that exceeds body temperature. For example, warm personal lubricant applied to the skin results in greater pore penetration than a personal lubricant applied to the skin at a temperature well below body temperature. The application of warm personal lubricant avoids the shock associated with a personal lubricant that has not been heated to a temperature that exceeds body temperature. In addition, the donning of a condom becomes a more pleasing experience if the condom is warm and easier if substantially more lubricated than a typical packaged condom known in the art. The temperature of the liquid material enclosed in a compartment may be monitored with the aid of a temperature sensor known in the art when the container is seated in a heating device. A compartment may comprise the temperature sensor or a component that makes contact with a temperature sensor a part of the heating apparatus.

By packaging condoms and personal lubricant in the manner disclosed above, a compartment may be heated independent of the other or heated to a different temperature than the other compartment. In the case of a container 10, if either compartment has been depleted, the depleted compartment may be removed and discarded without discarding the full or partially depleted compartment.

Because the contents of a compartment are not heated using an exothermic heat source the contents may be reheated. In addition the possibility exists that an exothermic heat source may contaminate the contents within a compartment when improperly activated.

The contents of a personal lubricant compartment 30 are discharged using a removable dispenser avoiding the mess associated with tearing open a package containing liquid material or dispensing the liquid material from a bottle either of which may be smeared with lubricant associated with a prior use. Alternatively, the contents of a personal lubricant compartment 30 are removed with the aid of a permanently attached dispenser 60.

The invention is tamper-proof and meets the highest of standards for personal hygiene. As regards tampering, the compartments are hermetically sealed. The condom compartment comprises a seal located on the top wall. When the seal is opened, the contents of the condom compartment are exposed and manually accessible. The personal lubricant compartment comprises a discharge element comprising multiple seals. The contents within the personal lubricant compartment are accessed and mechanically discharged rupturing a protective seal within the element using a dispenser. Preferably, a cap covering the discharge element is removed prior to rupturing the protective seal. Alternatively, the contents of the compartment are removed with the aid of a permanently attached dispenser. As regards personal hygiene, safeguards have been included which reduce the risk that liquid material contained in any previously accessed compartment will not migrate out. The condom compartment has two built-in safeguards. First, an opened condom compartment may be resealed by reattaching or closing the seal to the top wall. Second, a raised annular ring positioned on the top wall of the condom compartment provides a barrier to the migration of personal lubricant from the compartment when the compartment is positioned within a warming device. The personal lubricant compartment has built-in safeguards. First, a cap may be re-installed to the end of the discharge element. Second, the discharge element is sized to accommodate a dispenser that fits snugly within the element avoiding leakage. Finally, compartments comprising a container may be detached from one another. A previously accessed compartment may be detached avoiding a mess not otherwise solved.

The second embodiment of the combination condom and personal lubricant container 110 comprises two congruent personal lubricant compartments 130, 150. The personal lubricant contained in a congruent compartment 130 is half as much as that contained in a single personal lubricant compartment 30 shown in the first embodiment. As a result less liquid material is heated at any given time reducing the amount of times a lubricant is reheated.

CONCLUSION, RAMIFICATIONS, AND SCOPE

The invention is intended to encourage the use of condoms in sexual activities thereby reducing the spread of disease, including the human immunodeficiency virus (HIV), which may result in AIDS, and reducing the risk of pregnancy. Apart from its social purpose the invention also is intended enhance the sexual experience of adults. The invention should achieve these purposes.

Although the description above contains much specificity, it should not be construed as limiting the scope of the invention but merely providing illustrations of some of the embodiments of this invention. For example, the design and shape of the combination condom and personal lubricant container or the individual compartments and the design, shape, type and location of their components, including the various seals, discharge element, temperature sensing aid or raised annular ring, are not limited to the designs, shapes, types and locations shown in the drawings. For example, the depth of the condom compartment is depicted in the drawings as greater than that of the personal lubricant compartment. In fact, each compartment may be of equal depth or the personal lubricant compartment may be of greater depth than the condom compartment. The condom compartment may be of a shape other than cylindrical or rectangular. The top wall of the compartment may be in the shape of a half moon with a semi-cylindrical wall or other shape. For example, the temperature sensing aid may be located other than on the bottom wall of the condom or personal lubricant compartment. A temperature sensing aid may comprise any type of temperature sensor including but not limited to a thermistor, temperature probe or thermocouple or any other type of component as an aid in determining the temperature of the liquid material enclosed in a compartment when the container is seated in a warming device comprising a temperature sensor.

The scope of the invention should be determined by the appended claims and legal equivalents, rather than by the examples given.

What is claimed is:
1. A disposable combination condom and personal lubricant container comprising:
   a hermetically sealed condom compartment enclosing one or more condoms and a first personal lubricant, the condom compartment constructed of a packaging material which conducts heat to the first personal lubricant and comprising at least three walls wherein one of the walls is a top wall having a seal such that the one or more condoms can be removed from the compartment; and
   a hermetically sealed personal lubricant compartment defining an enclosure, a second personal lubricant disposed inside the enclosure, the personal lubricant compartment constructed of the packaging material which conducts heat to the second personal lubricant and comprising at least three walls wherein one of the walls is a top wall connected to the top wall of the condom compartment.

2. The container as recited in claim 1, wherein the personal lubricant compartment is removably connected to the condom compartment along a perforated edge between the top wall of the personal lubricant compartment and the top wall of the condom compartment.

3. The container as recited in claim 1, wherein the packaging material of the personal lubricant compartment transfers heat from a heating device to the second personal lubricant prior to removal of the second personal lubricant from the personal lubricant compartment.

4. The container as recited in claim 1, wherein the personal lubricant compartment further comprises a discharge element.

5. The container as recited in claim 4, wherein the discharge element further comprises a seal.

6. The container as recited in claim 5, wherein the discharge element comprises a cylindrical tube having a discharge end and a cap covering the discharge end.

7. The container as recited in claim 4, wherein the discharge element comprises an open-ended fitting through which the second personal lubricant within the personal lubricant compartment is discharged after rupturing a seal.

8. The container as recited in claim 4, wherein the discharge element comprises a permanently attached dispenser.

9. The container as recited in claim 1, wherein the seal of the condom compartment comprises a removable seal.

10. The container as recited in claim 9, wherein the removable seal is re-attachable.

11. The container as recited in claim 1, wherein the seal of the condom compartment is partially attached to the top wall of the condom compartment such that the condom compartment can be opened and closed without removing the seal from the top wall of the condom compartment.

12. The container as recited in claim 1, wherein the top wall of the condom compartment further comprises a raised annular ring positioned between a perimeter of the top wall of the condom compartment and the seal.

13. The container as recited in claim 1, further comprising a temperature sensing aid used to monitor a temperature of the one or more condoms or the first personal lubricant within the condom compartment.

14. The container as recited in claim 1, further comprising a temperature sensing aid used to monitor a temperature of the second personal lubricant within the personal lubricant compartment.

15. The container as recited in claim 1, wherein the packaging material of the condom compartment transfers heat from a heating device to the first personal lubricant prior to removal of the one or more condoms from the condom compartment.

* * * * *